US010619217B2

(12) United States Patent
Vogelstein et al.

(10) Patent No.: US 10,619,217 B2
(45) Date of Patent: *Apr. 14, 2020

(54) OLIGODENDROGLIOMA DRIVE GENES

(71) Applicants: The Johns Hopkins University, Baltimore, MD (US); Duke University, Durham, NC (US)

(72) Inventors: Bert Vogelstein, Baltimore, MD (US); Kenneth W. Kinzler, Baltimore, MD (US); Chetan Bettegowda, Baltimore, MD (US); Nishant Agrawal, Baltimore, MD (US); Nickolas Papadopoulos, Towson, MD (US); Darell Bigner, Mebane, NC (US); Hai Yan, Chapel Hill, NC (US); Roger McLendon, Durham, NC (US)

(73) Assignees: The Johns Hopkins University, Baltimore, MD (US); Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/834,886

(22) Filed: Dec. 7, 2017

(65) Prior Publication Data

US 2018/0195132 A1 Jul. 12, 2018

Related U.S. Application Data

(63) Continuation of application No. 14/233,296, filed as application No. PCT/US2012/047211 on Jul. 18, 2012, now Pat. No. 9,873,917.

(60) Provisional application No. 61/509,366, filed on Jul. 19, 2011.

(51) Int. Cl.
C12Q 1/68 (2018.01)
C12Q 1/6886 (2018.01)

(52) U.S. Cl.
CPC ..... *C12Q 1/6886* (2013.01); *C12Q 2600/106* (2013.01); *C12Q 2600/112* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 9,873,917 | B2 | 1/2018 | Vogelstein et al. |
| 2004/0053277 | A1 | 3/2004 | Zhang et al. |
| 2005/0255507 | A1 | 11/2005 | Jenkins et al. |
| 2010/0021590 | A1 | 1/2010 | Hartmann et al. |

FOREIGN PATENT DOCUMENTS

WO 2010028099 3/2010

OTHER PUBLICATIONS

Cairncross et al. (Journal of the National Cancer Institute, vol. 90, No. 19, Oct. 7, 1998, 1473-1479) (Year: 1998).*
Mardis eat al. (Human Molecular Genetics, 2009, vol. 18, Review Issue 2 R163-R168). (Year: 2009).*
Hegele (2002) Arterioscler Thromb Vas Biol, 22: 1058-1061 (Year: 2002).*
Sahm et al. Acta Neuropathol (2012) 123:853-860 (Year: 2012).*
Smith 2000. Journal of Clinical Oncology, vol. 18, No. 3 Feb. 2000; p. 636-645 (Year: 2000).*
Pennisi (1998) Science, New Series, vol. 281, No. 5384, p. 1787-1789 (Year: 1998).*
Lucentini (Dec. 2004) The Scientist, p. 20 (Year: 2004).*
Bettegowda, C. et al., 'Mutations in CIC and FUBP1 Contribute to Human Oligodendroglioma', Science, Sep. 9, 2011, vol. 333, pp. 1453-1455.
Sahm, F. et al., 'CIC and FUBP1 Mutations in Oligodendrogliomas, Oligoastrocytoma and Astrocytomas', Acta Neuropathol, May 17, 2012, vol. 123, pp. 853-860.
Yan, H. et al., 'IDH1 and IDH2 Mutations in Gliomas', The New England Journal of Medicine, Feb. 19, 2009, vol. 360, No. 8, pp. 765-773.
International Search Report and Written Opinion dated Jan. 28, 2013, for PCT/US2012/047211.
Extended European Search Report issued in related European Application No. 12814956.4, dated Feb. 13, 2015.
Lee et al., "CIC, a gene involved in cerebellar development and ErbB signaling, is significantly expressed in medulloblastomas," Journal of Neuro-Oncology, vol. 73, No. 2, Jun. 1, 2005, pp. 101-108.
Broderick et al. Cancer Research, 64, 5048-5050.
Reifenberger et al. (American Journal of Pathology, vol. 145, No. 5, Nov. 1994, pp. 1175-1190).
Hegele (2002) Arterioscler Thromb Vase Biol, 22:1-58-1061.
Pennisi (1998), Science, New Series, vol. 281, No. 5384, p. 1787-1789.

(Continued)

*Primary Examiner* — Juliet C Switzer

(74) *Attorney, Agent, or Firm* — Fish & Richardson P.C.

(57) ABSTRACT

Oligodendrogliomas are the second most common malignant brain tumor in adults. These tumors often contain a chromosomal abnormality involving a pericentromeric fusion of chromosomes 1 and 19, resulting in losses of the entire short arm of the former and the long arm of the latter. To identify the molecular genetic basis for this alteration, we performed exomic sequencing of seven anaplastic oligodendrogliomas with chromosome 1p and 19q losses. Among other changes, we found that that CIC (homolog of the *Drosophila* gene capicua) on chromosome 19q was somatically mutated in six of the seven cases and that FUBP1 (far upstream element (FUSE) binding protein) on chromosome 1p was somatically mutated in two of the seven cases. Examination of 27 additional oligodendrogliomas revealed 12 and 3 more tumors with mutations of CIC and FUBP1, respectively, 58% of which were predicted to result in truncations of the encoded proteins. These results suggest a critical role for these genes in the biology and pathology of oligodendrocytes.

6 Claims, 12 Drawing Sheets

Specification includes a Sequence Listing.

(56) References Cited

OTHER PUBLICATIONS

Lucentini (Dec. 2004) The Scientist, p. 20.
Coons et al., "Improving Diagnostic Accuracy and Interobserver Concordance fin the Classification and Grading of Primary Gilomas" cancer 79, 1381 (1997).
Bromberg et al., "Oligodendrogliomas: Molecular Biology and Treatment", Oncologist 14, 155 (2009).
Maintz et al., "Molecular Genetic Evidence for Subtypes of Oligoastrocytomas," J Nemopathol Exp Neuroi 56, 1098 (1997).
Smith et al., "Alterations of Chromosome Arms 1p and 19q as Predictors of Survival in Oligodendrogliomas, Astrocytomas, and Mixed Oligoastrocytomas," J Clin Oncol 18, 636 (2000).
Cairncross et al., "Gliomas With 1p/19q Codeletion: a.ka. Oligodendroglioma," Cancer J 14, 352 (2008).
Jenkins et al., "A t(1;19)(q10;p10) Mediates the combined Deletions of 1p and 19q and Predicts a Better Prognosis of Patients with Oligodendroglioma" Cancer Res 66, 9852 (2006).
Griffin et al., "Identification of der (1;19)(q10;p10) in Five Oligodendrogliomas Suggests Mechanism of Concurrent 1p and 19q Loss," J Neuropathol Exp Neurol 65, 988 (2006).
Bourne et al., "Update on Molecular Findings, Management, and Outcome in Low-grade Gliomas," Nat Rev Neurol 6, 695-701.
Knudson, Jr. et al., "The Genetics of Childhood Cancer," Cancer 35, 1022 (1975).
Sastre, "New DNA sequencing technologies open a promising era for cancer research and treatment," Clin Transl Oncol 13, 301-306.
Xi et al., "Detecting Structural Variations in the Human Genome Using Next Generation Sequencing," Brief Funct Genomics, 2011 9:405.
Bigner et al., "Molecular Genetic Aspects of Oligodendrogliomas Including Analysis by Comparative Genomic Hybridization," Arn J Pathol 155, 375 ( 1999).
Y. Jiao et al., DAXX/ATRX, MEN1 and mTOR pathway genes are frequently altered in pancreatic neuroendocrine tumors Science 331, 1199-1203 (2011).
Jones et al., "Frequent Mutations of Chromatin Remodeling Gene ARID1A in Ovarian Clear Cell Carcinoma," Science 330, 228 (2010).
Parsons et al., "An Integrated Genomic Analysis of Human Glioblastoma Multiforme," Science 321, 1807 (2008).
Samuels et al., "High Frequency of Mutations of the PIK3CA Gene in Human Cancers," Science 304, 554 (2004).
Vogt et al., "Phosphoinositide 3-kinase. From viral oncoprotein to drug target," Virology 344, 131 (2006).
Cantley, "The Phosphoinositide 3-Kinase Pathway" Science 296, 1655 (2002).
Samuels et al., "Oncogenic Mutations of PIK3CA in Human Cancers," Curr Top Microbiol Immunol, 2010 347, 21-41.
The Cancer Genome Atlas Research Nenvork, Nature 455, 1061 (2008).
Puente et al., "Non-coding recurrent mutations in chronic lymphocytic Leukaemia," Nature, 2015, 526:519-541.
H. Yan et al., "IDH1 and IDH2 Mutations in Gliomas," N Engl J Med 360, 765 (2009).
Yan et al., "Mutant Metabolic Enzymes Are at the Origin of Gliomas," Cancer Res 69, 9157 (2009).
Dang et al., "Cancer-associated IDH1 Mutations Produce 2-hydroxyglutarate," Nature 465, 966 (2010).
Knudson et al., "Hereditary cancer: two hits revisited," J. Cancer Res. Clin. OncoL 122, 135 (1996).
S. J. Baker et al., "Chromosome 17 Deletions and p53 Gene Mutations in Colorectal Carcinomas," Science 244, 217 (1989).
G. Parmigiani et al., "Design and Analysis Issues in Genome-Wide Somatic Mutation Studies of Cancer," Genomics in press, (2008).
Jimenez et al., "Relief of Gene Repression by Torso RTK Signaling: role of Capicua in *Drosophila* Terminal and Dorsoventral Patterning," Genes Dev 14, 224 (2000).
Garcia-Bellido et al., "Developmental Genetics of the Venation Pattern of *Drosophila*," Annu Rev Genet 26, 277 (1992).
Roch et al., "EGFR Signalling Inhibits Capicua-dependent Repression During Specification of *Drosophila* Wing Veins,", Development 129, 993 (2002).
Ajuria et al., "Capicua DNA-Binding Sites are General Response Elements for RTK Signaling in *Drosophila*," Development 138, 915.
Astigarraga et al., "a MAPK Docking Site is Critical for Downregulation of Capicua by Torso and EGFR RTK Signaling," EMBO J 26, 668 (2007).
Lee et al., "CIC, a gene involved in cerebellar development and ErbB signaling is significantly expressed in medulloblastomas," JNeurnoncol 73, 101 (2005).
Olsen et al., "Global, In Vivo, and Site-Specific Phosphorylation Dynamics in Signaling Networks," Cell 127, 635 (2006).
Wong et al., "Structural Alterations of the Epidermal Growth Factor Receptor Gene in Human Gliomas," Proc Natl Acad Sci US A 89, 2965 (1992).
Bigner et al., "Gene Amplification in Malignant Human Gilomas: Clinical and Histopathologic Aspects," JNeuropathol Exp Neurol 47, 191-205 (1988).
Vivanco et al., "Epiderman growth factor receptor inhibitors in oncology," 2010, Curr Opin Oncol 22, 573-578.
Duncan et al., "A sequence-specific, single-strand binding protein activates the far upstream element of c-,myc and defines a new DNA-binding motif," Genes Dev 8, 465 (1994).
Hsiao et al., Quantitative Characterization of the Interactions among c-myc Transcriptional Regulators FUSE, FBP, and FIR Biochemistry 49, 4620 (2010).
Kawamura-Saito et al., "Fusion between CIC and DUX4 up-regulates PEA3 family genes in Ewing-like Sarcomas with t(4;19)(q35;q13) Translocation," Hurn Mol Genet 15, 2125 (2006).
Grimwood et al., "The DNA sequence and biology of human chromosome 19," Nature 428, 529 (2004).

\* cited by examiner

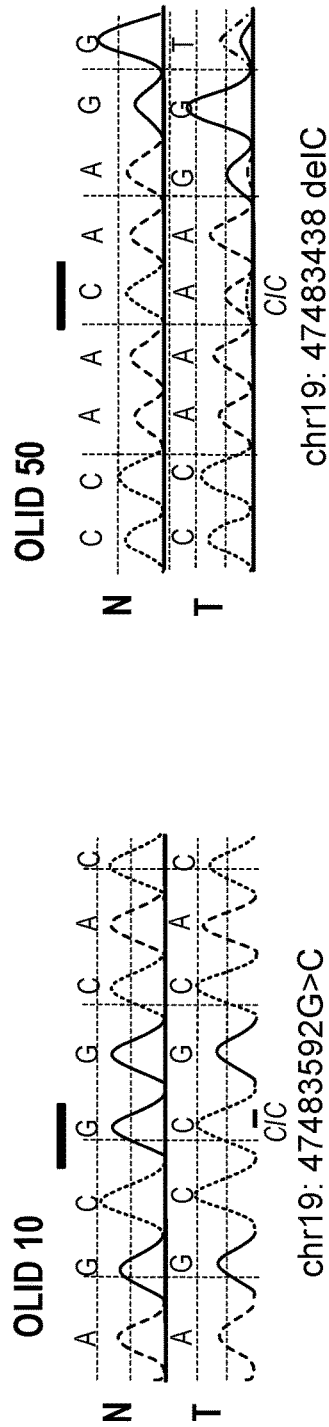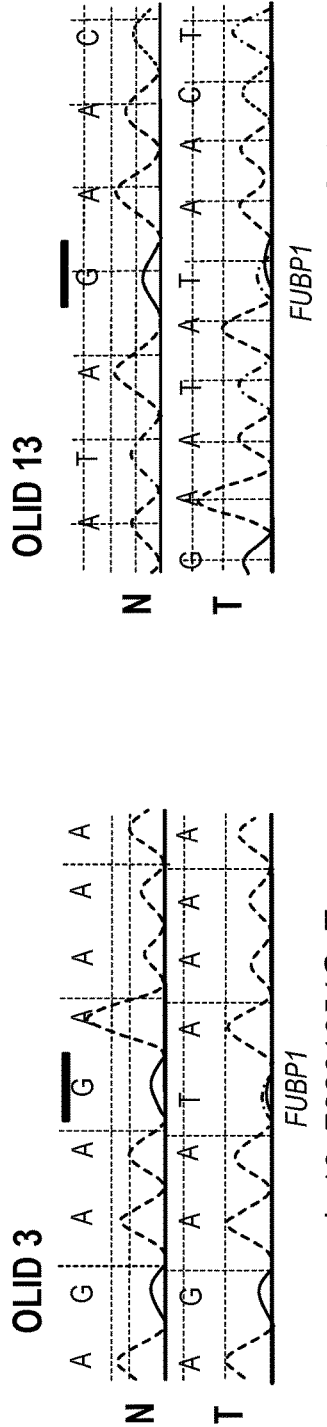
FIG. 2A
FIG. 2B

Fig. 4 Clinical characteristics of the patients and tumors

| Sample | Sex | Age | Race | Diagnosis | Experiment | CIC status | FUBP1 status |
|---|---|---|---|---|---|---|---|
| OLID 02 PT | M | 50 | White | Anaplastic oligodendroglioma | Discovery Screen | Mutant | WT |
| OLID 03 PT | M | 47 | White | Anaplastic oligodendroglioma | Validation | Mutant | Mutant |
| OLID 08 PT | M | 21 | White | Anaplastic oligodendroglioma | Discovery Screen | Mutant | WT |
| OLID 09 PT | M | 60 | White | Anaplastic oligodendroglioma | Discovery Screen | Mutant | Mutant |
| OLID 10 PT | F | 48 | White | Anaplastic oligodendroglioma | Discovery Screen | Mutant | WT |
| OLID 12 PT | M | 37 | White | Anaplastic oligodendroglioma | Discovery Screen | Mutant | WT |
| OLID 13 PT | M | 45 | Black | Anaplastic oligodendroglioma | Discovery Screen | Mutant | Mutant |
| OLID 15 PT | F | 65 | White | Anaplastic oligodendroglioma | Discovery Screen | WT | WT |
| OLID 21 PT | M | 21 | White | Oligodendroglioma | Discovery Screen | Mutant | WT |
| OLID 23 PT | M | 47 | Asian | Oligodendroglioma | Validation | WT | WT |
| OLID 26 PT | M | 50 | White | Oligodendroglioma | Validation | Mutant | WT |
| OLID 29 PT | F | 26 | Black | Oligodendroglioma | Validation | WT | WT |
| OLID 31 PT | M | 54 | White | Oligodendroglioma | Validation | WT | WT |
| OLID 32 PT | M | 25 | White | Anaplastic oligodendroglioma | Validation | WT | WT |
| OLID 33 PT | M | 59 | White | Anaplastic oligodendroglioma | Validation | WT | WT |
| OLID 34 PT | F | 52 | Black | Anaplastic oligodendroglioma | Validation | WT | WT |
| OLID 35 PT | M | 64 | White | Anaplastic oligodendroglioma | Validation | WT | WT |
| OLID 36 PT | M | 33 | White | Anaplastic oligodendroglioma | Validation | WT | WT |
| OLID 39 PT | M | 44 | White | Anaplastic oligodendroglioma | Validation | WT | WT |
| OLID 41 PT | M | 59 | White | Oligodendroglioma | Validation | WT | Mutant |
| OLID 42 PT | F | 45 | White | Oligodendroglioma | Validation | Mutant | WT |
| OLID 43 PT | M | 59 | White | Anaplastic oligodendroglioma | Validation | WT | WT |
| OLID 45 PT | M | 47 | White | Oligodendroglioma | Validation | Mutant | WT |
| OLID 48 PT | M | 50 | White | Oligodendroglioma | Validation | Mutant | WT |
| OLID 50 PT | M | 58 | White | Oligodendroglioma | Validation | Mutant | Mutant |
| OLID 55 PT | F | 49 | Hispanic | Anaplastic oligodendroglioma | Validation | Mutant | WT |
| OLID 57 PT | F | 34 | White | Oligodendroglioma | Validation | WT | WT |
| OLID 59 PT | F | 68 | White | Anaplastic oligodendroglioma | Validation | Mutant | WT |
| OLID 60 PT | F | 60 | White | Oligodendroglioma | Validation | Mutant | WT |
| OLID 61 PT | M | 50 | White | Oligodendroglioma | Validation | Mutant | WT |
| OLID 62 PT | M | 38 | White | Anaplastic oligodendroglioma | Validation | WT | WT |
| OLID 63 PT | M | 41 | White | Anaplastic oligodendroglioma | Validation | Mutant | WT |
| OLID 64 PT | F | 48 | White | Anaplastic oligodendroglioma | Validation | WT | WT |
| OLID 65 PT | M | 47 | White | Anaplastic oligodendroglioma | Validation | Mutant | WT |

Somatic mutations in oligodendrogliomas

Fig. 5

| Gene | Sample | Transcript Accession | Distinct WT reads | Distinct Mutant Reads | % Mutant Reads | Nucleotide (genomic) | Nucleotide (cDNA) | Amino acid (protein) | Mutation type |
|---|---|---|---|---|---|---|---|---|---|
| ABLIM3 | OLID10 | ENSG00000173210 | 62 | 30 | 33% | g.chr5:148543345G>T | c.151G>T | p.V51L | Missense |
| ACSM2B | OLID15 | ENSG00000066813 | 364 | 197 | 35% | g.chr16:20394591G>A | c.1093G>A | p.E365K | Missense |
| ACVR2A | OLID15 | ENSG00000121989 | 24 | 6 | 20% | g.chr2:148392614A>C | c.945A>C | p.K315N | Missense |
| ADAMTSL1 | OLID15 | ENSG00000178031 | 91 | 80 | 47% | g.chr9:18612389G>A | c.623G>A | p.R208Q | Missense |
| ADCY8 | OLID10 | ENSG00000155897 | 111 | 65 | 37% | g.chr8:131861858C>T | c.3716G>A | p.G1239E | Missense |
| AIM1 | OLID10 | ENSG00000112297 | 87 | 81 | 48% | g.chr6:107118399C>T | c.4982C>T | p.A1661V | Missense |
| ALDH1A2 | OLID09 | ENSG00000128918 | 132 | 81 | 38% | g.chr15:56074588C>G | c.535G>C | p.V179L | Missense |
| ALPI | OLID12 | ENSG00000163295 | 92 | 64 | 41% | g.chr2:233031230G>T | c.1051G>T | p.V351F | Missense |
| ANK3 | OLID15 | ENSG00000151150 | 23 | 13 | 36% | g.chr10:61492919C>T | c.12551G>A | p.R4184K | Missense |
| APOA5 | OLID12 | ENSG00000110243 | 185 | 70 | 27% | g.chr11:116166349C>T | c.806G>A | p.G269E | Missense |
| APOH | OLID10 | ENSG00000091583 | 139 | 93 | 40% | g.chr17:61654642G>A | c.199C>T | p.P67S | Missense |
| AQP7P1 | OLID13 | ENSG00000186466 | 24 | 7 | 23% | g.chr9:69963907G>A | c.200C>T | p.T67I | Missense |
| ARHGEF11 | OLID08 | ENSG00000132694 | 16 | 6 | 27% | g.chr1:155198194AGG> | c.-1CCT> | Splice Acceptor | Deletion |
| ARMC9 | OLID13 | ENSG00000135931 | 25 | 8 | 24% | g.chr2:231933783A>G | c.1138A>G | p.T380A | Missense |
| ARMC9 | OLID13 | ENSG00000135931 | 21 | 6 | 22% | g.chr2:231933784C>A | c.1139C>A | p.T380N | Missense |
| AWAT1 | OLID15 | ENSG00000204195 | 162 | 60 | 27% | g.chrX:69376795T>G | c.917T>G | p.L306R | Missense |
| BZRAP1 | OLID09 | ENSG00000005379 | 15 | 11 | 42% | g.chr17:53734738C>T | c.5614G>A | p.A1872T | Missense |
| C1RL | OLID15 | ENSG00000139178 | 177 | 155 | 47% | g.chr12:71401383C>T | c.1210G>A | p.A404T | Missense |
| C9 | OLID10 | ENSG00000113600 | 35 | 24 | 41% | g.chr5:39400250G>A | c.74C>T | p.T25I | Missense |
| CAPSL | OLID10 | ENSG00000152611 | 96 | 67 | 41% | g.chr5:35940462G>A | c.569C>T | p.A190V | Missense |
| CARD6 | OLID12 | ENSG00000132357 | 554 | 306 | 36% | g.chr5:40889659G>T | c.2468G>T | p.C823F | Missense |
| CASC1 | OLID02 | ENSG00000118307 | 61 | 42 | 41% | g.chr12:25205320C>G | c.100G>C | p.E34Q | Missense |
| CCDC46 | OLID15 | ENSG00000154240 | 27 | 25 | 48% | g.chr17:61328743G>A | c.2152C>T | p.R718X | Nonsense |
| CCKAR | OLID02 | ENSG00000163394 | 32 | 18 | 36% | g.chr4:26096443G>C | c.540C>G | p.S180R | Missense |
| CDH15 | OLID10 | ENSG00000129910 | 56 | 44 | 44% | g.chr16:87777488C>G | c.389C>G | p.S130C | Missense |
| CDKN2C | OLID02 | ENSG00000123080 | 9 | 32 | 78% | g.chr1:51208631delG | c.3delG | fs | Deletion |
| CELSR1 | OLID02 | ENSG00000075275 | 25 | 9 | 26% | g.chr22:45238402C>T | c.4049G>A | p.R1350H | Missense |
| CIC | OLID09 | ENSG00000079432 | 18 | 116 | 87% | g.chr19:47483555C>T | c.601C>T | p.R201W | Missense |
| CIC | OLID10 | ENSG00000079432 | 11 | 103 | 90% | g.chr19:47483592G>C | c.638G>C | p.R213P | Missense |
| CIC | OLID12 | ENSG00000079432 | 47 | 89 | 65% | g.chr19:47483598G>A | c.644G>A | p.R215Q | Missense |
| CIC | OLID08 | ENSG00000079432 | 19 | 47 | 71% | g.chr19:47486574delGT | c.1814delGT | fs | Deletion |
| CIC | OLID15 | ENSG00000079432 | 8 | 84 | 91% | g.chr19:47487549G>A | IVS10-1G>A | Splice Acceptor | Missense |
| CIC | OLID02 | ENSG00000079432 | 10 | 35 | 78% | g.chr19:47490688G>T | c.4420G>T | p.V1474F | Missense |
| CLEC10A | OLID08 | ENSG00000132514 | 171 | 104 | 38% | g.chr17:69208011G>C | c.317C>G | p.A106G | Missense |
| COL4A6 | OLID10 | ENSG00000197565 | 39 | 28 | 42% | g.chrX:107310478G>T | c.2057C>A | p.T686N | Missense |
| CTBP2 | OLID02 | ENSG00000175029 | 11 | 8 | 42% | g.chr10:126705043C>T | c.1276G>A | p.V426M | Missense |

Fig. 5 cont'd

| | | | | | | | |
|---|---|---|---|---|---|---|---|
| CTRB1 | OLID15 | ENSG00000168925 | 128 | 113 | 47% | g.chr16:738162361T>C | c.763T>C | p.W255R | Missense |
| CTTNBP2 | OLID15 | ENSG00000077063 | 15 | 10 | 40% | g.chr7:117300675C>T | c.31G>A | p.D11N | Missense |
| DLGAP4 | OLID15 | ENSG00000080845 | 153 | 101 | 40% | g.chr20:345585506G>T | c.1677G>T | p.K559N | Missense |
| DOCK1 | OLID12 | ENSG00000150760 | 88 | 54 | 38% | g.chr10:128720390G>A | c.-1G>A | Splice Acceptor | Nonsense |
| DPP4 | OLID12 | ENSG00000197635 | 112 | 62 | 36% | g.chr2:162589643G>A | c.940C>T | p.Q314X | Nonsense |
| ESPNP | OLID10 | ENSG00000116219 | 12 | 10 | 45% | g.chr1:169067113insAGCT | c.660insAGCT | fs | Insertion |
| ETFDH | OLID08 | ENSG00000171503 | 4 | 19 | 83% | g.chr4:159836147G>C | c.733G>C | p.A245P | Missense |
| EXO1 | OLID09 | ENSG00000174371 | 39 | 62 | 61% | g.chr1:240096852A>G | c.1139A>G | p.E380G | Missense |
| FAM189B | OLID13 | ENSG00000160767 | 8 | 11 | 58% | g.chr1:153486973G>C | c.1228C>G | p.P410A | Missense |
| FAM81B | OLID09 | ENSG00000153347 | 100 | 86 | 46% | g.chr5:94781846C>T | c.640C>T | p.R214X | Nonsense |
| FBN3 | OLID02 | ENSG00000142449 | 54 | 48 | 47% | g.chr19:80568977C>T | c.6463G>A | p.G2155S | Missense |
| FMNL1 | OLID09 | ENSG00000184922 | 128 | 104 | 45% | g.chr17:40679373C>A | c.3104C>A | p.A1035D | Missense |
| FOXE1 | OLID02 | ENSG00000178919 | 4 | 7 | 64% | g.chr9:99656603G>A | c.586G>A | p.V196I | Missense |
| FTSJ1 | OLID15 | ENSG00000068438 | 96 | 34 | 26% | g.chrX:48224780C>T | c.491C>T | p.T164M | Missense |
| FTSJ3 | OLID08 | ENSG00000108592 | 135 | 57 | 30% | g.chr17:59255751delCT | c.994delAG | fs | Deletion |
| FUBP1 | OLID09 | ENSG00000162613 | 4 | 16 | 80% | g.chr1:78198726delG | c.1538delC | fs | Deletion |
| FUBP1 | OLID13 | ENSG00000162613 | 30 | 13 | 30% | g.chr1:78201156C>A | c.1231G>T | p.E411X | Nonsense |
| GFPT2 | OLID02 | ENSG00000131459 | 40 | 31 | 44% | g.chr5:179661205G>A | c.2014C>T | p.P672S | Missense |
| GP5 | OLID02 | ENSG00000178732 | 16 | 10 | 38% | g.chr3:195598934G>A | c.1367C>T | p.A456V | Missense |
| GPR50 | OLID15 | ENSG00000102195 | 206 | 103 | 33% | g.chrX:150099372A>T | c.659A>T | p.D220V | Missense |
| GPR98 | OLID12 | ENSG00000164199 | 53 | 27 | 34% | g.chr5:90042869G>A | c.9016G>A | p.G3006R | Missense |
| GSC2 | OLID12 | ENSG00000063515 | 23 | 15 | 39% | g.chr22:17517331G>A | c.358C>T | p.P120S | Missense |
| HCLS1 | OLID02 | ENSG00000180353 | 48 | 44 | 48% | g.chr3:122833438C>T | c.1406G>A | p.R469H | Missense |
| HDAC2 | OLID15 | ENSG00000196591 | 73 | 65 | 47% | g.chr6:114376895T>G | c.1064A>C | p.Q355P | Missense |
| HDAC2 | OLID15 | ENSG00000196591 | 62 | 51 | 45% | g.chr6:114381231C>A | c.824G>T | p.G275V | Missense |
| HERC2P3 | OLID08 | ENSG00000180229 | 0 | 12 | 100% | g.chr15:189265594C>T | c.49G>A | p.V17I | Missense |
| HHAT | OLID02 | ENSG00000054392 | 66 | 46 | 41% | g.chr1:208704582C>T | c.967C>T | p.R323C | Missense |
| HIST1H2BA | OLID09 | ENSG00000146047 | 144 | 46 | 24% | g.chr6:25835416C>T | c.301C>T | p.R101C | Missense |
| HMCN1 | OLID02 | ENSG00000143341 | 35 | 28 | 44% | g.chr1:184289631G>T | c.6752G>T | p.G2251V | Missense |
| HMOX1 | OLID09 | ENSG00000100292 | 241 | 235 | 49% | g.chr22:34119521C>T | c.797C>T | p.P266L | Missense |
| HNF1A | OLID13 | ENSG00000135100 | 92 | 36 | 28% | g.chr12:119911194C>T | c.502C>T | p.R168C | Missense |
| HOXB1 | OLID09 | ENSG00000120094 | 68 | 55 | 45% | g.chr17:43962757G>A | c.509C>T | p.S170L | Missense |
| HUWE1 | OLID15 | ENSG00000086758 | 73 | 20 | 22% | g.chrX:53579186A>G | c.12533T>C | p.V4178A | Missense |
| IDH1 | OLID02 | ENSG00000138413 | 36 | 25 | 41% | g.chr2:208821357C>T | c.395G>A | p.R132H | Missense |
| IDH1 | OLID08 | ENSG00000138413 | 30 | 21 | 41% | g.chr2:208821357C>T | c.395G>A | p.R132H | Missense |
| IDH1 | OLID09 | ENSG00000138413 | 68 | 30 | 31% | g.chr2:208821357C>T | c.395G>A | p.R132H | Missense |
| IDH1 | OLID10 | ENSG00000138413 | 66 | 40 | 38% | g.chr2:208821357C>T | c.395G>A | p.R132H | Missense |
| IDH1 | OLID12 | ENSG00000138413 | 57 | 32 | 36% | g.chr2:208821357C>T | c.395G>A | p.R132H | Missense |
| IDH1 | OLID13 | ENSG00000138413 | 67 | 44 | 40% | g.chr2:208821357C>T | c.395G>A | p.R132H | Missense |
| IDH1 | OLID15 | ENSG00000138413 | 86 | 54 | 39% | g.chr2:208821357C>T | c.395G>A | p.R132H | Missense |

Fig. 5 cont'd

| Gene | OLID | ENSG | | | | | | |
|---|---|---|---|---|---|---|---|---|
| IL16 | OLID08 | ENSG00000172349 | 29 | 28 | 49% | g.chr15:79305012A>C | c.217A>C | p.S73R | Missense |
| ILDR1 | OLID12 | ENSG00000145103 | 92 | 33 | 26% | g.chr3:123206826C>T | c.334G>A | p.V112M | Missense |
| ITGA9 | OLID15 | ENSG00000144668 | 71 | 36 | 34% | g.chr3:37670231G>T | c.1862G>T | p.R621L | Missense |
| JAGN1 | OLID15 | ENSG00000171135 | 80 | 65 | 45% | g.chr3:9909633T>C | c.124T>C | p.Y42H | Missense |
| KCNIP4 | OLID15 | ENSG00000185774 | 80 | 69 | 46% | g.chr4:20594580A>C | c.67T>G | p.S23A | Missense |
| KCNK10 | OLID08 | ENSG00000100433 | 54 | 38 | 41% | g.chr14:87763610G>C | c.543C>G | p.S181R | Missense |
| KIAA0146 | OLID15 | ENSG00000164808 | 140 | 84 | 38% | g.chr8:48515494A>G | c.934A>G | p.M312V | Missense |
| KIAA1024 | OLID15 | ENSG00000169330 | 314 | 185 | 37% | g.chr15:77536425C>T | c.881C>T | p.P294L | Missense |
| KIAA1267 | OLID15 | ENSG00000120071 | 62 | 55 | 47% | g.chr17:41464894C>T | c.3113G>A | p.R1038Q | Missense |
| KLF17 | OLID12 | ENSG00000171872 | 93 | 41 | 31% | g.chr1:44368372G>T | c.842G>T | p.R281M | Missense |
| KRT6A | OLID02 | ENSG00000205420 | 147 | 66 | 31% | g.chr12:51170651C>T | c.1046G>A | p.R349Q | Missense |
| LAMB1 | OLID13 | ENSG00000091136 | 257 | 100 | 28% | g.chr7:107387008C>A | c.2612G>T | p.G871V | Missense |
| LILRB3 | OLID02 | ENSG00000204577 | 25 | 10 | 29% | g.chr19:59436674C>A | c.800G>T | p.R267L | Missense |
| LNX2 | OLID12 | ENSG00000139517 | 92 | 56 | 38% | g.chr13:27032118C>T | c.1229G>A | p.S410N | Missense |
| LRRC16B | OLID09 | ENSG00000186648 | 121 | 100 | 45% | g.chr14:23607708G>A | c.3758G>A | p.G1253E | Missense |
| MAF1 | OLID13 | ENSG00000179632 | 109 | 73 | 40% | g.chr8:145233053T>G | c.299T>G | p.L100R | Missense |
| MAP3K6 | OLID08 | ENSG00000142733 | 5 | 21 | 81% | g.chr1:27557293G>A | c.2881C>T | p.R961C | Missense |
| MARK2 | OLID12 | ENSG00000072518 | 27 | 7 | 21% | g.chr11:63414276G>T | c.47G>T | p.C16F | Missense |
| MGAT4C | OLID02 | ENSG00000182050 | 23 | 14 | 38% | g.chr12:84898298C>A | c.337G>T | p.G113X | Nonsense |
| MGEA5 | OLID02 | ENSG00000198408 | 40 | 38 | 49% | g.chr10:103542618A>G | c.2143T>C | p.Y715H | Missense |
| MSH6 | OLID13 | ENSG00000116062 | 333 | 133 | 29% | g.chr2:47879705G>A | c.1079G>A | p.S360N | Missense |
| MTMR1 | OLID15 | ENSG00000063601 | 52 | 15 | 22% | g.chrX:149651745A>T | c.941A>T | p.D314V | Missense |
| MTSS1 | OLID09 | ENSG00000170873 | 69 | 19 | 22% | g.chr8:125634913C>T | c.1769G>A | p.R590Q | Missense |
| MUC17 | OLID02 | ENSG00000169876 | 152 | 101 | 40% | g.chr7:100468283C>T | c.6866C>T | p.T2289M | Missense |
| MXI1 | OLID08 | ENSG00000119950 | 22 | 10 | 31% | g.chr10:111957822delAAAAC | c.266delAAAAC | fs | Deletion |
| MYH1 | OLID15 | ENSG00000109061 | 183 | 150 | 45% | g.chr17:10346907T>C | c.2984A>G | p.K995R | Missense |
| MYT1 | OLID10 | ENSG00000196132 | 94 | 54 | 36% | g.chr20:62329690C>G | c.2597C>G | p.S866C | Missense |
| NAB2 | OLID09 | ENSG00000166886 | 23 | 44 | 66% | g.chr12:57711635C>T | c.544C>T | p.P182S | Missense |
| NDUFAF2 | OLID02 | ENSG00000164182 | 5 | 7 | 58% | g.chr5:60276855G>T | c.16G>T | p.D6Y | Missense |
| NEO1 | OLID02 | ENSG00000067141 | 99 | 28 | 22% | g.chr15:71362504A>T | c.3409A>T | p.K1137X | Nonsense |
| NF1 | OLID13 | ENSG00000196712 | 166 | 56 | 25% | g.chr17:26586864delCT | c.3818delCT | fs | Deletion |
| NKD2 | OLID09 | ENSG00000145506 | 45 | 26 | 37% | g.chr5:1087967G>A | c.523G>A | p.V175I | Missense |
| NOS1 | OLID15 | ENSG00000089250 | 35 | 27 | 44% | g.chr12:116207495G>A | c.1316C>T | p.T439M | Missense |
| NOTCH1 | OLID10 | ENSG00000148400 | 10 | 17 | 63% | g.chr9:138529574delG | c.2113delC | fs | Deletion |
| NOTCH1 | OLID15 | ENSG00000148400 | 3 | 27 | 90% | g.chr9:138532891AGA> | c.1303TCT> | In-frame deletion, 5 bp | Deletion |
| NOTCH2 | OLID10 | ENSG00000134250 | 38 | 19 | 33% | g.chr1:120285672delCT | c.3208delAG | fs | Deletion |
| NOTCH2 | OLID08 | ENSG00000134250 | 10 | 9 | 47% | g.chr1:120413487G>C | c.57C>G | p.C19W | Missense |
| NOTCH2 | OLID10 | ENSG00000134250 | 19 | 13 | 41% | g.chr1:120413526delGG | c.89delCC | fs | Deletion |
| NOTCH2NL | OLID10 | ENSG00000213240 | 7 | 7 | 22% | g.chr1:143920548G>C | c.86G>C | p.R29P | Missense |
| NUP188 | OLID02 | ENSG00000095319 | 52 | 41 | 44% | g.chr9:130772927C>G | c.982C>G | p.L328V | Missense |

Fig. 5 cont'd

| | | | | | | | | |
|---|---|---|---|---|---|---|---|---|
| ODC1 | OLID08 | ENSG00000115758 | 75 | 73 | 49% | g.chr2:105017739C>A | c.382G>T | p.V128F | Missense |
| OFD1 | OLID02 | ENSG00000046651 | 5 | 29 | 85% | g.chrX:13680758A>G | c.1070A>G | p.H357R | Missense |
| OR6C76 | OLID02 | ENSG00000185821 | 51 | 33 | 39% | g.chr12:54106812G>A | c.508G>A | p.V170I | Missense |
| OSBPL3 | OLID10 | ENSG00000070882 | 57 | 60 | 51% | g.chr7:24810559C>T | c.2467G>A | p.E823K | Missense |
| PCBP2 | OLID08 | ENSG00000197111 | 27 | 17 | 39% | g.chr12:52151711G>A | c.905G>A | p.R302H | Missense |
| PDCD6IP | OLID10 | ENSG00000170248 | 43 | 36 | 46% | g.chr3:33869114A>G | c.1772A>G | p.D591G | Missense |
| PDE4C | OLID10 | ENSG00000105650 | 192 | 57 | 23% | g.chr19:18190304C>T | c.1070G>A | p.R357Q | Missense |
| PHKA2 | OLID15 | ENSG00000044446 | 153 | 52 | 25% | g.chrX:18911928G>A | c.44C>T | p.A15V | Missense |
| PIK3CA | OLID12 | ENSG00000121879 | 53 | 22 | 29% | g.chr3:180404247T>A | c.1035T>A | p.N345K | Missense |
| PIK3CA | OLID02 | ENSG00000121879 | 18 | 13 | 42% | g.chr3:180418785G>A | c.1633G>A | p.E545K | Missense |
| PIK3CA | OLID09 | ENSG00000121879 | 30 | 26 | 46% | g.chr3:180418785G>A | c.1633G>A | p.E545K | Missense |
| PIK3R1 | OLID15 | ENSG00000145675 | 38 | 27 | 42% | g.chr5:67624979TAA> | c.1211TAA> | In-frame deletion, 3 bp | Deletion |
| PLXNA3 | OLID15 | ENSG00000130827 | 145 | 54 | 27% | g.chrX:153342312G>A | c.-1G>A | Splice Donor | Missense |
| POTEJ | OLID10 | ENSG00000222038 | 22 | 6 | 21% | g.chr2:131085722G>C | c.147G>C | p.Q49H | Missense |
| PPAPDC3 | OLID02 | ENSG00000160539 | 27 | 26 | 49% | g.chr9:133155516C>T | c.311C>T | p.A104V | Missense |
| PRAMEF5 | OLID15 | ENSG00000204502 | 7 | 6 | 46% | g.chr1:13238574A>G | c.431A>G | p.Q144R | Missense |
| PRDM9 | OLID09 | ENSG00000164256 | 131 | 87 | 40% | g.chr5:23560216C>T | c.967C>T | p.R323W | Missense |
| PRIM2 | OLID12 | ENSG00000146143 | 199 | 57 | 22% | g.chr6:57506130C>T | c.874C>T | p.H292Y | Missense |
| PRR5 | OLID08 | ENSG00000186654 | 13 | 17 | 57% | g.chr22:43600095G>A | c.647G>A | p.R216Q | Missense |
| PRR5-ARHGAP8 | OLID08 | ENSG00000186654 | 13 | 17 | 57% | g.chr22:43600095G>A | c.647G>A | p.R216Q | Missense |
| PSENEN | OLID09 | ENSG00000205155 | 28 | 110 | 80% | g.chr19:40929503G>A | c.221G>A | p.W74X | Nonsense |
| PTPRZ1 | OLID10 | ENSG00000106278 | 152 | 103 | 40% | g.chr7:121439304delCT | c.2968delCT | fs | Deletion |
| PUM1 | OLID09 | ENSG00000134644 | 158 | 86 | 35% | g.chr1:31199197C>T | c.2542G>A | p.E848K | Missense |
| RAB3IP | OLID10 | ENSG00000127328 | 30 | 30 | 50% | g.chr12:68481758G>A | c.1168G>A | p.G390R | Missense |
| RBBP6 | OLID09 | ENSG00000122257 | 33 | 15 | 31% | g.chr16:24472381TA> | c.-1TA> | Splice Donor | Deletion |
| RBL2 | OLID12 | ENSG00000103479 | 111 | 65 | 37% | g.chr16:52072012A>G | c.2914A>G | p.S972G | Missense |
| RBPJ | OLID08 | ENSG00000168214 | 8 | 20 | 71% | g.chr4:26026195G>T | c.195G>T | p.R65S | Missense |
| RGPD3 | OLID09 | ENSG00000153165 | 57 | 22 | 28% | g.chr2:106415824T>A | c.2468A>T | p.K823M | Missense |
| RIMKLB | OLID12 | ENSG00000166532 | 45 | 18 | 29% | g.chr12:8797816A>T | c.557A>T | p.H186L | Missense |
| RNF138 | OLID15 | ENSG00000134758 | 40 | 29 | 42% | g.chr18:27963093A>G | c.683A>G | p.D228G | Missense |
| ROBO2 | OLID12 | ENSG00000185008 | 140 | 47 | 25% | g.chr3:77230157C>T | c.364C>T | p.R122X | Nonsense |
| RP1 | OLID02 | ENSG00000104237 | 18 | 12 | 40% | g.chr8:55701679T>C | c.2684T>C | p.L895S | Missense |
| RPUSD4 | OLID09 | ENSG00000165526 | 102 | 39 | 28% | g.chr11:125580585G>A | c.784C>T | p.Q262X | Nonsense |
| SETD5 | OLID10 | ENSG00000168137 | 51 | 29 | 36% | g.chr3:9459995C>T | c.1081C>T | p.R361X | Nonsense |
| SHROOM3 | OLID15 | ENSG00000138771 | 11 | 13 | 54% | g.chr4:77881603G>A | c.3250G>A | p.A1084T | Missense |
| SI | OLID09 | ENSG00000090402 | 37 | 10 | 21% | g.chr3:166259519C>T | c.1324G>A | p.A442T | Missense |
| SLC19A2 | OLID12 | ENSG00000117479 | 100 | 58 | 37% | g.chr1:167705837G>A | c.1019C>T | p.S340L | Missense |
| SLC22A12 | OLID02 | ENSG00000197891 | 21 | 18 | 46% | g.chr11:64115915C>T | c.311C>T | p.T104M | Missense |
| SLC39A12 | OLID02 | ENSG00000148482 | 22 | 11 | 33% | g.chr10:18320206T>C | c.1390T>C | p.C464R | Missense |
| SLC9A6 | OLID15 | ENSG00000198689 | 27 | 13 | 33% | g.chrX:134926479C>T | c.1246C>T | p.L416F | Missense |

Fig. 5 cont'd

| Gene | Sample | Ensembl/NM | col4 | col5 | col6 | Genomic | cDNA | Protein | Type |
|---|---|---|---|---|---|---|---|---|---|
| SMCR7 | OLID12 | ENSG00000177427 | 93 | 60 | 39% | g.chr17:181108505T>G | c.1067T>G | p.L356R | Missense |
| TBC1D12 | OLID12 | ENSG00000108239 | 11 | 8 | 42% | g.chr10:96153297C>T | c.937C>T | p.R313X | Nonsense |
| TCEA2 | OLID09 | ENSG00000171703 | 17 | 20 | 54% | g.chr20:62172419G>A | c.806G>A | p.C269Y | Missense |
| TJP2 | OLID12 | ENSG00000119139 | 65 | 39 | 38% | g.chr9:71051444C>G | c.2585C>G | p.S862X | Nonsense |
| TLN1 | OLID09 | ENSG00000137076 | 100 | 93 | 48% | g.chr9:35690267T>C | c.6581A>G | p.N2194S | Missense |
| TMEM138 | OLID09 | ENSG00000149483 | 278 | 200 | 42% | g.chr11:60891977C>T | c.307C>T | p.R103C | Missense |
| TMEM90A | OLID12 | ENSG00000183379 | 68 | 28 | 29% | g.chr14:73946173G>A | c.28C>T | p.P10S | Missense |
| TP63 | OLID13 | ENSG00000073282 | 56 | 54 | 49% | g.chr3:191107929G>A | c.1659G>A | p.W553X | Nonsense |
| TRPV2 | OLID12 | ENSG00000187688 | 169 | 132 | 44% | g.chr17:16272939C>T | c.1505C>T | p.A502V | Missense |
| TTLL3 | OLID12 | ENSG00000214021 | 142 | 41 | 22% | g.chr3:9849888G>A | c.1655G>A | p.R552H | Missense |
| TTN | OLID02 | ENSG00000155657 | 30 | 33 | 52% | g.chr2:179288726T>A | c.21928A>T | p.K7310X | Nonsense |
| UBASH3A | OLID10 | ENSG00000160185 | 74 | 60 | 45% | g.chr21:42699503C>T | c.131C>T | p.A44V | Missense |
| UGT2B17 | OLID15 | ENSG00000197888 | 22 | 211 | 91% | g.chr4:69116635C>A | c.163G>T | p.V55L | Missense |
| UNC5B | OLID12 | ENSG00000107731 | 122 | 60 | 33% | g.chr10:72721449C>T | c.1549C>T | p.R517W | Missense |
| UNC93B1 | OLID15 | ENSG00000110057 | 18 | 9 | 33% | g.chr11:67515772A>C | c.1612T>G | p.Y538D | Missense |
| UNC93B5 | OLID15 | ENSG00000184795 | 13 | 8 | 38% | g.chr4:9108557C>G | c.451C>G | p.Q151E | Missense |
| UNC93B5 | OLID13 | ENSG00000184795 | 8 | 8 | 50% | g.chr4:9108578G>A | c.472G>A | p.V158M | Missense |
| USP6 | OLID10 | ENSG00000129204 | 21 | 8 | 28% | g.chr17:4976998C>A | c.265C>A | p.H89N | Missense |
| USP7 | OLID09 | ENSG00000187555 | 67 | 48 | 42% | g.chr16:8918411C>T | c.824G>A | p.G275E | Missense |
| UTP20 | OLID10 | ENSG00000120800 | 105 | 86 | 45% | g.chr12:100256096C>T | c.3778C>T | p.L1260F | Missense |
| VPS37D | OLID15 | ENSG00000176428 | 70 | 50 | 42% | g.chr7:72723343C>T | c.457C>T | p.R153C | Missense |
| WASH1 | OLID09 | ENSG00000181404 | 20 | 6 | 23% | g.chr16:6539A>G | c.920T>C | p.V307A | Missense |
| WASH3P | OLID15 | ENSG00000185596 | 4 | 7 | 64% | g.chr15:100330725delC | c.360delC | fs | Deletion |
| WDR45L | OLID15 | ENSG00000141580 | 96 | 71 | 43% | g.chr17:78172910G>A | c.482C>T | p.T161M | Missense |
| WDR61 | OLID13 | ENSG00000140395 | 85 | 39 | 31% | g.chr15:76367774C>T | c.568G>A | p.A190T | Missense |
| WNT10B | OLID09 | ENSG00000169884 | 66 | 34 | 34% | g.chr12:47648001G>A | c.706C>T | p.R236C | Missense |
| WNT4 | OLID02 | ENSG00000162552 | 22 | 69 | 76% | g.chr1:22328439C>T | c.436G>A | p.V146M | Missense |
| XPOT | OLID10 | ENSG00000184575 | 47 | 15 | 24% | g.chr12:63100443C>T | c.718C>T | p.R240W | Missense |
| ZFP36L2 | OLID02 | ENSG00000152518 | 37 | 27 | 42% | g.chr2:43305919G>T | c.528C>A | p.F176L | Missense |
| ZNF23 | OLID12 | ENSG00000167377 | 81 | 42 | 34% | g.chr16:70039826T>C | c.1603A>G | p.M535V | Missense |
| ZNF532 | OLID02 | ENSG00000074657 | 11 | 39 | 78% | g.chr18:54802182A>T | c.-1A>T | Splice Acceptor | Missense |
| ZNF626 | OLID09 | ENSG00000188171 | 23 | 7 | 23% | g.chr19:20599019T>A | c.1504A>T | p.I502F | Missense |
|  | OLID10 | NM_1333447 | 160 | 125 | 44% | g.chr10:88759505C>A | c.1516C>A | p.L506I | Missense |
|  | OLID12 | NM_020373 | 86 | 32 | 27% | g.chr11:5320448T>C | c.883A>G | p.K295E | Missense |
|  | OLID15 | NM_014191 | 77 | 58 | 43% | g.chr12:58098870T>A | c.820A>T | p.S274C | Missense |
|  | OLID08 | NM_001109754 | 65 | 51 | 44% | g.chr12:50385483G>A | c.1150G>A | p.G384R | Missense |
|  | OLID02 | NM_001098519 | 127 | 104 | 45% | g.chr12:69251270G>C | c.3173C>G | p.S1058X | Nonsense |
|  | OLID10 | NM_015473 | 30 | 17 | 36% | g.chr12:121236750G>A | c.472G>A | p.A158T | Missense |
|  | OLID15 | NM_015473 | 181 | 115 | 39% | g.chr14:30913773C>A | c.982G>T | p.A328S | Missense |
|  | OLID12 | NM_001134875 | 18 | 12 | 40% | g.chr14:105036195T>G | c.1148T>G | p.I383S | Missense |

Fig. 5 cont'd

| | | | | | | | |
|---|---|---|---|---|---|---|---|
| OLID10 | ENSG00000188388 | 28 | 11 | 28% | g.chr15:83586491C>T | c.121C>T | p.P41S | Missense |
| OLID12 | ENSG00000205125 | 20 | 12 | 38% | g.chr15:100112051C>G | c.4C>G | p.Q2E | Missense |
| OLID13 | ENSG00000169203 | 18 | 6 | 25% | g.chr16:29406018A>G | c.118T>C | p.W40R | Missense |
| OLID15 | ENSG00000178130 | 133 | 100 | 43% | g.chr17:21749634A>G | c.7A>G | p.K3E | Missense |
| OLID15 | ENSG00000178130 | 81 | 81 | 50% | g.chr17:21749676T>A | c.49T>A | p.F17I | Missense |
| OLID02 | ENSG00000214553 | 110 | 82 | 43% | g.chr17:34441817C>T | c.602C>T | p.P201L | Missense |
| OLID15 | NM_025185 | 302 | 240 | 44% | g.chr17:58846718T>A | c.3866T>A | p.L1289Q | Missense |
| OLID12 | NM_001142966 | 68 | 54 | 44% | g.chr18:17288429G>A | c.2089G>A | p.D697N | Missense |
| OLID02 | ENSG00000105663 | 6 | 29 | 83% | g.chr19:40916548G>A | c.7094G>A | p.G2365D | Missense |
| OLID15 | ENSG00000168129 | 125 | 103 | 45% | g.chr2:82937620A>G | c.160A>G | p.M54V | Missense |
| OLID13 | NM_001370 | 41 | 28 | 41% | g.chr2:847388970G>A | c.5801G>A | p.R1934H | Missense |
| OLID09 | ENSG00000214329 | 42 | 11 | 21% | g.chr2:91444175A>G | c.673T>C | p.F225L | Missense |
| OLID10 | NM_015672 | 64 | 22 | 26% | g.chr22:18837634G>A | c.3668C>T | p.P1223L | Missense |
| OLID13 | ENSG00000169662 | 27 | 7 | 21% | g.chr22:19976619C>T | c.97G>A | p.D33N | Missense |
| OLID02 | ENSG00000169892 | 19 | 6 | 24% | g.chr22:19993645C>T | c.88G>A | p.A30T | Missense |
| OLID02 | NM_015175 | 17 | 16 | 48% | g.chr3:47014171G>A | c.2941G>A | p.G981R | Missense |
| OLID02 | NM_178554 | 57 | 47 | 45% | g.chr3:135805344G>C | c.1753C>G | p.L585V | Missense |
| OLID02 | NM_015236 | 33 | 76 | 70% | g.chr4:62618805C>A | c.3994C>A | p.P1332T | Missense |
| OLID02 | NM_015236 | 13 | 32 | 71% | g.chr4:62619215T>G | c.4404T>G | p.S1468R | Missense |
| OLID02 | NM_002092 | 22 | 50 | 69% | g.chr4:71916189T>C | c.881A>G | p.Y294C | Missense |
| OLID12 | ENSG00000204644 | 61 | 41 | 40% | g.chr6:29751222G>A | c.212C>T | p.P71L | Missense |
| OLID02 | ENSG00000196306 | 12 | 7 | 37% | g.chr6:29963574C>T | c.67C>T | p.Q23X | Nonsense |
| OLID09 | ENSG00000168477 | 5 | 7 | 58% | g.chr6:321634464G>A | c.2801C>T | p.T934M | Missense |
| OLID10 | NM_001145118 | 125 | 111 | 47% | g.chr7:6520630G>A | c.1324C>T | p.Q442X | Nonsense |
| OLID15 | NM_012294 | 23 | 7 | 23% | g.chr7:222297388A> | c.-1T> | Splice Acceptor | Deletion |
| OLID09 | NM_001164462 | 15 | 6 | 29% | g.chr7:100426040C>T | c.5476C>T | p.H1826Y | Missense |
| OLID08 | ENSG00000221917 | 9 | 6 | 40% | g.chr9:68722517A>T | c.44A>T | p.D15V | Missense |
| OLID08 | ENSG00000221917 | 11 | 6 | 35% | g.chr9:68722526G>A | c.53G>A | p.G18E | Missense |
| OLID08 | ENSG00000221917 | 19 | 6 | 24% | g.chr9:68729866C>G | c.130C>G | p.Q44E | Missense |

Fig. 6

Mutations identified in the validation samples

| Sample | Gene | Transcript Accession | Nucleotide (genomic) | Nucleotide (cDNA) | Amino Acid (protein) | Mutation Type |
|---|---|---|---|---|---|---|
| OLID 03PT | CIC | CCDS12601.1 | chr19:47485924insG | c.1445insG | fs | Insertion |
| OLID 23PT | CIC | CCDS12601.1 | chr19:47490903delAGA | c.4547delAGA | p.QK1517RD | Deletion |
| OLID 42PT | CIC | CCDS12601.1 | chr19:47483711G>GA | c.757G>GA | p.A253T | Missense |
| OLID 45PT | CIC | CCDS12601.1 | chr19:47490722C>CT | c.4454C>CT | p.P1485L | Missense |
| OLID 48PT | CIC | CCDS12601.1 | chr19:47483597C>CT | c.643C>CT | p.R215RW | Missense |
| OLID 50PT | CIC | CCDS12601.1 | chr19:47483438delC | c.579delC | fs | Deletion |
| OLID 55PT | CIC | CCDS12601.1 | chr19:47483952G>GA | c.916G>GA | p.A306T | Missense |
| OLID 59PT | CIC | CCDS12601.1 | chr19:47490203delCGCAAGATGAGAAGACG | c.4234delCGCAAGATGAGAAGACG | fs | Deletion |
| OLID 60PT | CIC | CCDS12601.1 | chr19:47483597C>CT | c.643C>CT | p.R215W | Missense |
| OLID 61PT | CIC | CCDS12601.1 | chr19:47483597C>CT | c.643C>CT | p.R215W | Missense |
| OLID 63PT | CIC | CCDS12601.1 | chr19:47483597C>T | c.643C>T | p.R215W | Missense |
| OLID 65PT | CIC | CCDS12601.1 | chr19:47490728G>GC | IVS44594+1 | Splice Site | Splice Site |
| OLID 03PT | FUBP1 | CCDS683.1 | chr1:78201054G>GT | c.1333G>GT | p.E445X | Nonsense |
| OLID 41PT | FUBP1 | CCDS683.1 | chr1:78206433delACTG | c.248delACTG | fs | Deletion |
| OLID 50PT | FUBP1 | CCDS683.1 | chr1:78193600delG | c.1708delG | fs | Deletion |

OLIGODENDROGLIOMA DRIVE GENES

STATEMENT OF FEDERALLY SPONSORED RESEARCH

This invention was made with government support under Grant No. CA43460, awarded by the National Institutes of Health. The government has certain rights in the invention.

TECHNICAL FIELD OF THE INVENTION

This invention is related to the area of cancer. In particular, it relates to brain cancers.

BACKGROUND OF THE INVENTION

Oligodendrogliomas (ODs) account for 20% of brain tumors in adults and, as their name suggests, they have prominent oligodendroglial differentiation (1, 2). These tumors generally arise in the white matter of cerebral hemispheres, in the frontal lobes. Well-differentiated ODs can evolve into high-grade "anaplastic" ODs, though it is often difficult to clearly distinguish these two types from each other or from other brain tumors (1, 2). Because this distinction is important for the management of patients, molecular biomarkers for ODs are of great interest.

To date, the best biomarker for ODs is loss of heterozygosity (LOH) of chromosomes 1p and 19q (2-5). Assessment for LOH events is now commonly performed in patients with ODs because of their important implications for therapeutic responses (2-5). The chromosome losses occur in 50% to 70% of tumors and are often associated with a pericentromeric translocation of chromosomes 1 and 19, producing marker chromosome der(1;19) (q10;p10) (2-7). This translocation is unbalanced, leaving the cells with one copy of the short arm of chromosome 1 and one copy of the long arm of chromosome 19. The functional basis for most cancer translocations involves one of the genes residing near the breakpoints, producing fusions that alter the gene's product. In contrast, the der(1;19) (q10;p10) breakpoints are in gene-poor centromeric regions and are always associated with LOH (4, 6, 8). This suggests that the basis for the t(1;19) translocation is the unmasking of a tumor suppressor gene(s) on either chromosome 1p or 19q (2-5), (9). This is supported by the fact that some tumors lose only chromosome 1p sequences, while others lose only chromosome 19q sequences.

There is a continuing need in the art to identify this putative tumor suppressor gene(s), as well as to increase understanding of OD pathogenesis.

SUMMARY OF THE INVENTION

One aspect of the invention is a method of identifying an oligodendroglioma. A sample is tested for an inactivating mutation in CIC, FUBP1, or both CC and FUBP. The sample is from a brain tissue suspected of being a brain tumor, or in cells or nucleic acids shed from the tumor. The presence of the inactivating mutation indicates an oligodendroglioma.

Another aspect of the invention is a method of stratifying a patient with a brain tumor. A sample is tested for an inactivating mutation of CIC. The sample is from a brain tumor or cells or nucleic acids shed from the tumor. Brain tumors with the mutation are refractory to EGFR inhibitors.

Yet another aspect of the invention is a method of predicting survival for a patient with an oligodendroglioma. A sample is tested for an inactivating mutation in CIC, FUBP1 or both CIC and FUBP1. The sample is from the oligodendroglioma or cells or nucleic acids shed from the oligodendroglioma. Presence of the mutation portends an improved survival relative to oligodendroglioma patients without the inactivation mutation. Absence of the mutation portends a decreased survival relative to oligodendroglioma patients with the inactivation mutation.

Still another aspect of the invention is a method of predicting chemotherapy response or radiotherapy response of an oligodendroglioma. A sample is tested for an inactivating mutation in CIC, FUBP1 or both CIC and FUBP1 in the oligodendroglioma. Presence of the inactivating mutation portends a positive response to chemotherapy or radiotherapy. Absence of the inactivating mutation portends a negative response to chemotherapy or radiotherapy.

One aspect of the invention is a method of monitoring status of a patient with a brain tumor that has an inactivating mutation in CIC, FUBP1 or both CIC and FUBP1. A sample of blood or cerebrospinal fluid from the patient is tested to determine an amount of nucleic acids with an inactivating mutation in CIC, FUBP1 or both CIC and FUBP. The step of testing is repeated one or more times with samples taken at distinct time points. An increase in the amount of the nucleic acids indicates an increase in the amount of brain tumor. A decrease in the amount of the nucleic acids indicates a decrease in the amount of brain tumor. An equivalent amount of the nucleic acids indicates an equivalent amount of brain tumor.

These and other embodiments which will be apparent to those of skill in the art upon reading the specification provide the art with tools for diagnosis, prognosis, treatment, and assessment of brain cancers.

BRIEF DESCRIPTION OF THE DRAWINGS

(FIG. 1A) In tumor OLID 13, the estimated LOH on chromosome 1 extends from base 901,779 to base 148,526,024 and the estimated LOH on chromosome 19 extends from base 18,116,940 to base 62,357,562. (FIG. 1B) In tumor OLID 09, the estimated LOH on chromosome 1 extends from base 1,844,406 to base 110,751,800, the estimated LOH on chromosome 9 extends from base 108,032 to base 20,875,240 and the estimated LOH on chromosome 19 extends from base 18,545,563 to base 62,923,619. The "minor allele" of each SNP represents the allele that was less common in the tumor. If both alleles of the SNP were represented by an equal number of tags, the minor allele fraction would be represented as 100% on the y-axis. The remaining signals in the regions exhibiting LOH represent contaminating non-neoplastic cells in the samples.

FIG. 2A-FIG. 2B Mutations in CIC and FUBP1. (FIG. 2A) Sanger sequencing chromatograms showing representative CIC or FUBP1 mutations in the indicated tumors. T, DNA from tumor; N, DNA from matched normal tissue. The mutated bases are overlined with a red bar. (FIG. 2B) Mutation distribution of CIC mutations. Red arrows represent missense mutations substitutions, black arrows represent insertions or deletions, and green arrows represent splice site alterations. See Tables s2 and s3 for details. The black boxes denote exons, Pro-rich denotes the proline-rich domains, HMG denotes the high mobility group domain, and the start and stop codons are indicated.

(FIG. 3A) In tumor OLID 2, the estimated LOH on chromosome 1 extends from base 1,640,705 to base 113,038,204, on chromosome 4 from base 41,310,447 to base 187,775,127, on chromosome 9 from base 10,47,204 to base 17,263,878, on chromosome 13 from base 24,254,053 to base 102,272,383, on chromosome 15 from base 27,202,852 to base 89,313,271, on chromosome 18 from base 6,975,631 to base 58,781,511 and the estimated LOH on chromosome 19 extends from base 18,835,200 to base 63,681,236. (FIG. 3B) In tumor OLID 8, the estimated LOH on chromosome 1 extends from base 1,640,705 to base 112,100,105, on chromosome 4 from base 1,077,531 to base 186,509,767, on chromosome 9 from base 123,968,827 to base 138,453,090 and the estimated LOH on chromosome 19 extends from base 17,525,418 to base 62,340,089. (FIG. 3C) In tumor OLID 15, the estimated LOH on chromosome 1 extends from base 1,129,725 to base 111,695,481, on chromosome 9 from base 115,970,015 to base 139,897,127 and the estimated LOH on chromosome 19 extends from base 17,589,502 to base 61,645,775. (FIG. 3D) In tumor OLID 10, the estimated LOH on chromosome 1 extends from base 1,640,705 to base 120,413,529, on chromosome 9 from base 108,032 to base 138,820,929 and the estimated LOH on chromosome 19 extends from base 18,146,944 to base 62,601,639. (FIG. 3E) In tumor OLID 12, the estimated LOH on chromosome 1 extends from base 939,471 to base 111,767,814, on chromosome 4 from base 3,008,948 to base 186,509,767, on chromosome 9 from base 2,707,698 to base 38,005,327, on chromosome 15 from base 22,879,808 to base 97,285,457 and the estimated LOH on chromosome 19 extends from base 22,048,143 to base 63,560,292.

FIG. 4 (Table s1) Clinical characteristics of the patients and tumors

FIG. 5 (Table s2) Somatic mutations in oligodendrogliomas

FIG. 6 (Table s3) Mutations identified in the validation samples

DETAILED DESCRIPTION OF THE INVENTION

Figure 1A:
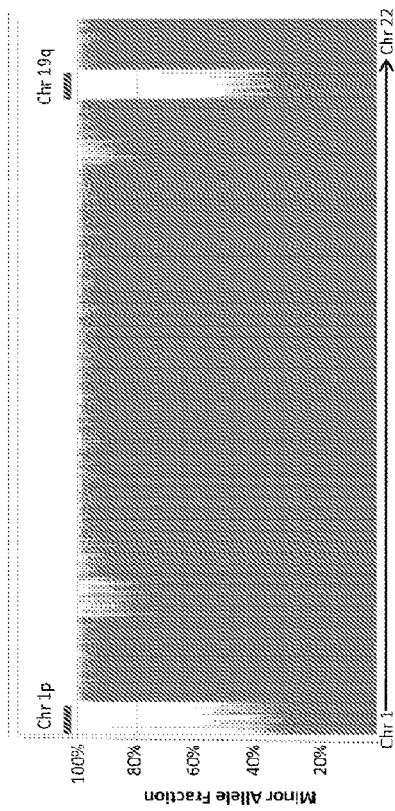
FIG. 1A-FIG. 1B. Loss of heterozygosity (LOH) maps of two representative tumors.

The inventors have developed methods for identifying, stratifying, prognosing, theranosing, and monitoring brain tumors, particularly oligodendrogliomas. The methods center around two genes which were found to be frequently mutated in such brain tumors, CIC and FUBP1. Mutations of many types have been found. The spectrum of mutations indicates that the mutations inactivate the gene products, identifying the genes as tumor suppressors.

Tests for CIC and FUBP1 mutations can be performed using protein based or nucleic based assays. Sequence determination of the nucleic acid can be used to identify mutations. Probes or primers, and kits and techniques employing both can be used. PCR or other specific or global amplification can be used. Mutations can be identified in any available genetic material including, for example, genomic DNA, cDNA, and RNA. Nucleic acids can be amplified, enriched, and/or purified prior to assessment. Protein based assays may involve specific antibodies and/or CIC and FUBP1 binding partners such as PUF60. The antibodies may be polyclonal or monoclonal, fragments (Fab, Fab'), single chain constructs (scFv), etc. Nucleic acid based assays include without limitation, hybridization to probes, amplification using specific primers, primer extension, ligation assay, etc. Any of these techniques can also be combined. Assays can be performed together with tests for other gene mutations or alterations of the genome. Results can be integrated and used to accurately and comprehensively characterize and/or identify a tumor or the patient.

Results of assays can be recorded in a written medium, an electronic medium, or transmitted orally or electronically to a health care provider, a patient, a family member, a hospital, a medical record, etc. Testing requires physical steps, and typically involves chemical changes to occur to a test sample. Typically the test sample is a sample that is removed from the patient body, so that the test is performed outside of a patient body.

Samples which may be tested include without limitation brain tissue, tumor tissue, CNS fluid, neuronal tissue, blood, urine, saliva, tears, sputum, etc. These samples may be collected and processed and/or stored prior to testing. For example, serum or plasma samples derived from blood may be used in an assay. The samples may be frozen or fixed. They may be archival or freshly collected.

Any type of mutation may be identified. Inactivating mutations include without limitation CIC mutations in the genome g.chr19:47483555C>T; g.chr19:47483592G>C; g.chr19:47483598G>A; g.chr19:47486574delGT; g.chr19:47487549G>A; g.chr19:47490688G>T; g.chr19:47485924-insG; g.chr19:47490903delAGA; g.chr19:47483711G>A; g.chr19:47490722C>T; g.chr19:47483597C>T; g.chr19:47483438delC; g.chr19:47483952G>A; g.chr19:47490203delCGCAAGATGAGAAGACG (SEQ ID NO: 1); and g.chr19:47490728G>GC; CIC mutations in cDNA c.601C>T; c.638G>C; c.644G>A; c.1814delGT; IVS10-1G>A; c.4420G>T; c.1445insG; c.4547delAGA; c.757G>A; c.4454C>T; c.643C>T; c.579delC; c.916G>A; c.4234delCGCAAGATGAGAAGACG (SEQ ID NO: 1); c.643C>T; and IVS4459+1. The mutation may be a frameshift mutation, a splice-site mutation, an indel (insertion or deletion) mutation, or a missense mutation. Particular mutations which may be identified include p.R201W; p.R213P; p.R215Q; p.QK1517RD; p.A253T; p.P1485L; p.A306T; p.R215W; and p.V1474F.

Inactivating mutations in FUBP1 include without limitation genomic mutations chr1:78201054G>T; chr1:78206439delACTG; chr1:78193600delG; g.chr1:78198726delG; g.chr1:78201156C>A, and mutations in the cDNA at c.1333G>T; c.248delACTG; c.1538delC; c.1231G>T; c.1708delG. The mutation may be a nonsense, deletion, or frameshift, for example. Particular mutations include p.E445X and p.E411X.

Stratification of patients can be used to assign a treatment regimen. It may be used in prospective or retrospective clinical studies. It can be used to assign a prognosis or a prediction regarding survival or chemotherapy or radiotherapy sensitivity. Stratification typically assigns a patient to a group based on a shared mutation pattern or other observed characteristic or set of characteristics.

Predictions of survival can be based on one or more characteristic of a disease or patient having the disease. Predictions based on one characteristic can be modified by other characteristics, making the predictions more accurate. The characteristic inactivating mutations in CIC and FUBP1 can be used individually or in combination with each other or with other characteristics. Predictions of survival rates or times can be communicated and/or recorded for the patient, other health care professionals, the medical record of the patient, the patient's family, etc. Such predictions are typically made by comparing survival data for a group of patients that share one or more characteristics with the patient.

The mutations in CIC and FUBP1 can be similarly used to design a treatment plan. The treatment plan can take into consideration which drugs or other therapies are typically effective in tumors with these mutations and which drugs or other therapies are typically ineffective. Thus the mutation status can be used to make a decision to treat or a decision not to treat with a particular agent.

A brain tumor, such as an oligodendroglioma, can be monitored over time using the nucleic acids with the CIC and FUBP1 mutations as a marker of the tumor. The monitoring can be used as a means to detect recurrence, or growth and progression of an existing tumor. The monitoring can be used to measure response to a therapeutic regimen. At least two time points are assessed so that changes over time can be determined. Any suitable control sample can be used for means of normalizing results. These may include a non-cancer specific nucleic acid marker, such as a housekeeping gene, or wild-type versions of the CIC and FUBP1 genes, or the total amount of nucleic acids. Those of skill in the art will recognize best ways to normalize the data.

The capicua gene was discovered in a screen for mutations affecting the anteroposterior pattern of *Drosophila* embryos (29). Females with inactivating CIC mutations produce embryos that form head and tail structures but lack most intervening segments (capicua means "head-and-tail" in Catalan). In *Drosophila*, the protein encoded by CIC has been shown to be a downstream component of receptor tyrosine kinase (RTK) pathways that includes EGFR, Torso, Ras, Raf, and mitogen-associated protein kinases (MAPKs) (30, 31). In the absence of RTK signaling, cic, in combination with other transcription factors such as Groucho (Gro), blocks transcription by binding to canonical octameric elements in regulatory regions (32). RTK signaling blocks the function of cic via MAPK-mediated phosphorylation or docking, resulting in degradation of cic and the consequent activation of the genes it normally represses (33). The most highly conserved functional domain of the cic protein is the HMG (high mobility group) box responsible for its binding to DNA. Importantly, 8 of the 11 missense mutations we observed in ODs were located in this domain (FIG. 2B).

In addition to the high conservation of CIC sequences among metazoans, the human cic protein contains nine consensus phosphorylation sites for MAPK(34). This suggests that human cic functions similarly to its *Drosophila* counterpart. This hypothesis is supported by mass spectroscopic studies that have shown human cic protein to be phosphorylated within 10 minutes of EGF treatment of HeLa cells (35). Genetic alterations of EGFR are common in glioblastomas (36, 37), prompting clinical trials of EGFR inhibitors (38). However, epistatic experiments in *Drosophila* (31) show that that cic is downstream of EGFR, suggesting that EGFR inhibitors would not be useful in ODs with CIC mutations.

The protein encoded by FUBP1 binds to single stranded DNA, in particular the far-upstream element (FUSE) of MYC, a well-studied oncogene (39). Although overexpression of FUBP1 can stimulate MYC expression (39), it has also been shown that FUBP1 protein participates in a complex with PUF60 that negatively regulates MYC expression (40). Our data, showing that FUBP1 is inactivated by mutations, are consistent with the idea that FUBP1 mutations lead to MYC activation in these tumors by relieving the negative effects of the FUBP1-PUF60-FUSE complex.

There are only a small and statistically insignificant number of point mutations of FUBP1 or CIC recorded in the COSMIC database (41). However, CIC has shown to be translocated in two cases of Ewing's sarcoma-like tumors that harbored t(4;19)(q35;q13) translocations. Unlike the mutations observed in ODs, the translocations in these two cases seemed to activate the cic protein by fusing it to the C-terminus of DUX4, conferring oncogenic properties to the new protein (42).

Overall, 23 mutations of CIC or FUBP1 were identified in the 34 tumors analyzed in this study. As our mutational screens would not detect some types of inactivating mutations (e.g., large deletions or promoter mutations) or epigenetic alterations, the fraction of tumors with detectable CIC and FUBP1 mutations is likely an underestimate of their actual contribution.

How do the der(1;19) (q10;p10) chromosomes arise? One possibility is that the pericentromeric translocation of chromosomes 1 and 19 is facile way to inactivate CIC given the high homology between the centromeres of these two chromosomes (43). In this scenario, the unbalanced translocation event would be solely driven by CIC inactivation. Inactivation of tumor suppressor genes on 1p, such as FUBP1, NOTCH2, MAP3KC, and CDKN2C (FIG. 5; Table s2) would then represent opportunistic events in a subset of the tumors with CIC mutations. However, the fact that two of five ODs with FUBP1 mutations did not have detectable CIC mutations argues against this model. The converse situation, in which the initial driver event is an inactivation of FUBP1, subsequently followed in some cases by mutational inactivation of CIC, is therefore also possible. These scenarios are consistent with the demonstration that losses of chromosome 1p do not always occur in conjunction with losses of chromosome 19, and vice versa (2-5). Regardless of the chain of events, our identification of inactivating mutations of CIC or FUBP1 in a substantial fraction of ODs are likely to provide important insights into the pathogenesis of these tumors as well as help refine their diagnosis, prognosis, and treatment options.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

We sequenced the coding exons of 20,687 genes in DNA from seven anaplastic ODs and compared them to the sequences of DNA from normal leukocytes of the same patients. All seven tumors had been shown to have LOH of chromosome 1p and 19q using approved clinical assays. The clinical characteristics of the patients and their tumors are listed in FIG. 4; Table s1. DNA from enriched neoplastic cells and matched normal cells was sheared and used to prepare fragment libraries suitable for massively parallel sequencing (10). The coding sequences of the targeted genes were captured with the 50 MB SureSelect Enrichment System and sequenced using the Illumina HiSeq platform. The average coverage of each base in the targeted regions was high (135-fold), and 94% of the bases were represented by at least 10 reads (Table 1).

Table 1A and 1B: Summary of Sequence Analysis of Oligodendrogliomas

TABLE 1A

| Coverage Summary | Tumor | Normal |
| --- | --- | --- |
| Bases sequenced (after quality filtering) | $12.3 \pm 4.0 \times 10^9$ | $11.8 \pm 1.3 \times 10^9$ |

TABLE 1A-continued

| Coverage Summary | Tumor | Normal |
|---|---|---|
| Bases mapped to targeted region | 7.36 ± 2.3 × 10$^9$ | 7.32 ± 0.82 × 10$^9$ |
| Average # of reads per targeted base | 135 ± 42.2 | 135 ± 12.2 |
| Targeted bases with at least 10 reads (%) | 94 ± 1.1% | 95 ± 0.5% |

TABLE 1B

| Tumor and normal comparison | |
|---|---|
| Known SNPs identified in tumor | 22,817 ± 1083 |
| % tumor SNPs identified in matched normal | 99.7 ± 0.02% |
| Non-synonymous somatic mutations in tumor | 32.1 ± 10.7 |

Figure 1B:
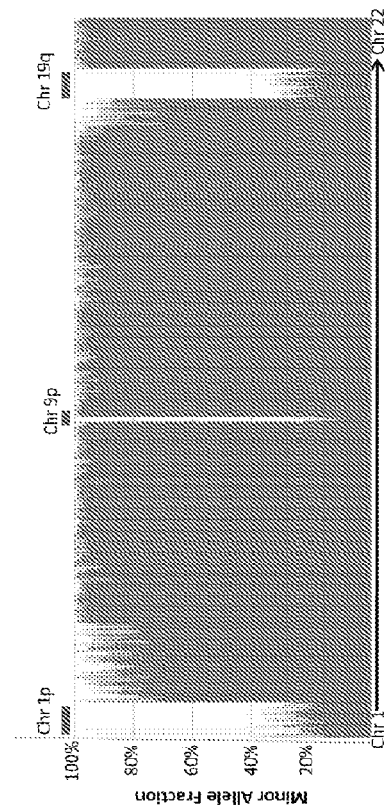
Figure 3A:
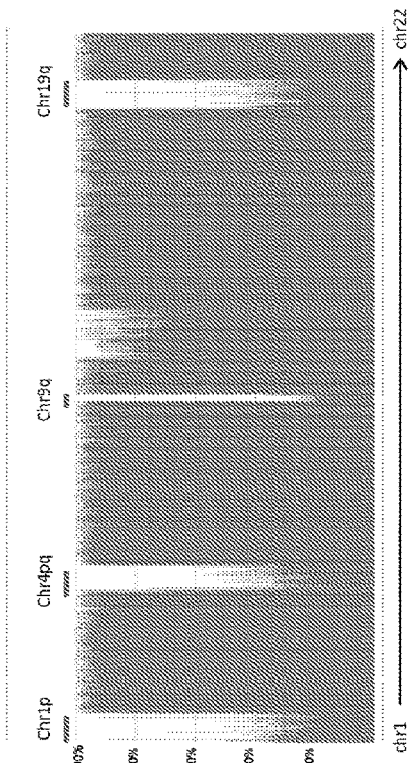
FIG. 3A-3E (Fig. s1) Loss of heterozygosity (LOH) maps of the remaining discovery screen samples.
Figure 3B:
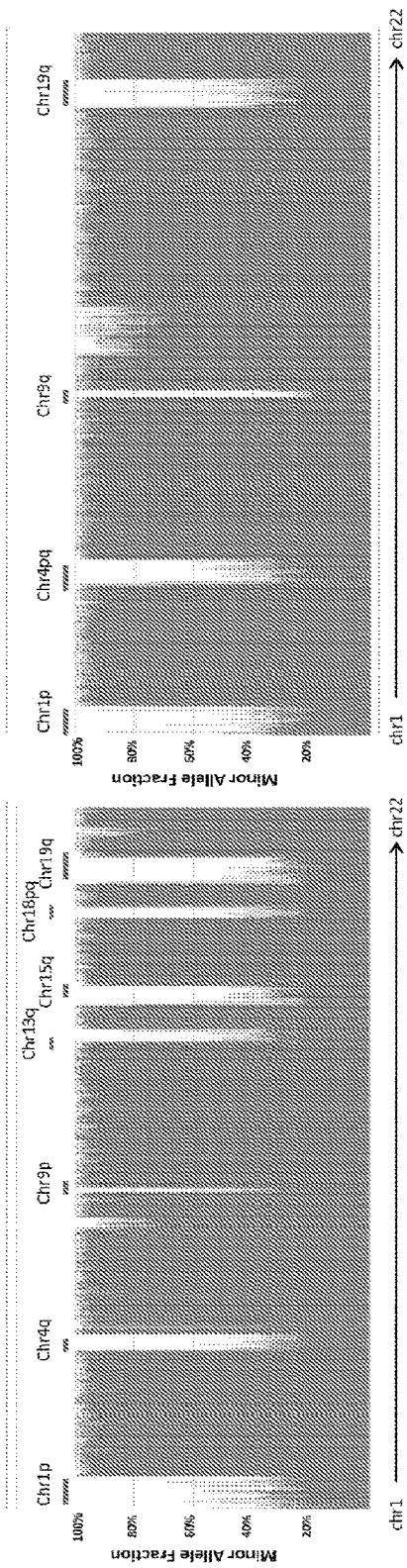
Figure 3C:
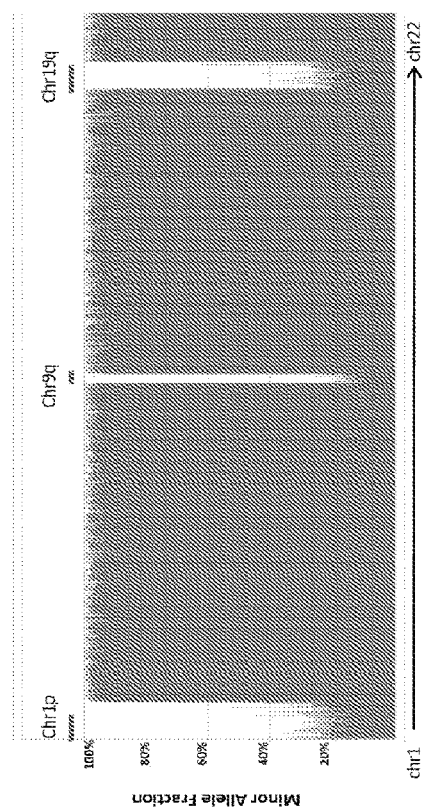
Figure 3D:
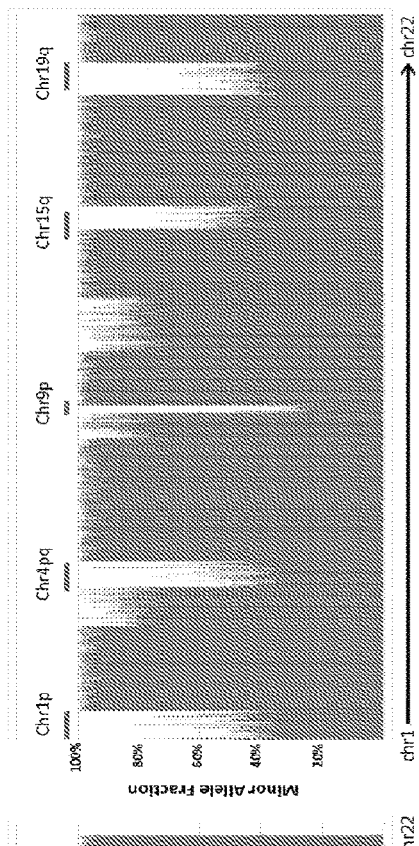
Figure 3E:
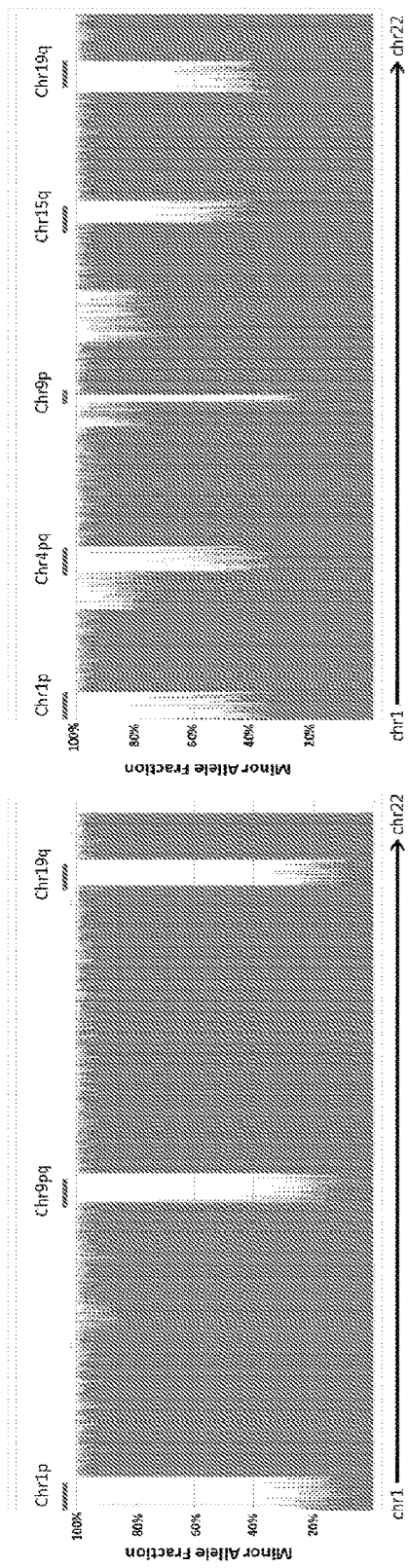

As with complete genomic sequencing (11, 12), exomic sequencing can identify chromosomal regions that undergo loss of heterozygosity (LOH) using common single nucleotide polymorphisms (SNPs) identified to be heterozygous in DNA from corresponding normal cells. There were 14,032±540 SNPs per patient that could be used for this analysis. An example is provided in FIG. 1A, indicating that the only regions exhibiting LOH in tumor OLID 13 were on chromosomes 1p and 19q. Another example is in FIG. 1B, showing that tumor OLID 09 had lost loci on chromosomes 9p as well as 1p and 19q. LOH on chromosome 9p occurs in a third of ODs and likely reflects inactivation of the CDKN2A tumor suppressor gene (13). All seven ODs analyzed by genomic sequencing exhibited LOH of alleles spanning the entire short arm of chromosome 1 and the entire long arm of chromosome 19 (FIG. 3 (s1)). Other recurrent changes were on chromosome 9p (four tumors), 4q (three tumors), and 15q (two tumors) (FIG. 3 (s1)).

Example 2

We have previously described methods for the accurate identification of somatic mutations in next-generation sequencing data from Illumina instruments (14, 15). Using these stringent criteria to avoid false positive calls, we identified a total of 225 non-synonymous somatic mutations, affecting 200 genes, among the seven tumors (FIG. 5; FIG. 5; Table s2). There were an average of 32.1±10.7 non-synonymous somatic mutations per tumor (Table 1), similar to the number found in the most common type of adult brain tumor (glioblastoma, 35.6 non-synonymous somatic mutations per tumor (16)).

There were a number of notable mutations identified in these seven tumors. Three tumors with mutations in PIK3CA were identified, each occurring in a previously defined "hotspot" for recurrent mutations in other tumor types (FIG. 5; Table s2) (17). PIK3CA encodes the catalytic subunit of the PI3Kα lipid kinase (18-20). A fourth tumor had a 3-base pair deletion in PIK3R1, the gene encoding the regulatory subunit of the PI3Kα enzyme; in-frame deletions of PIK3R1 are relatively common in other types of brain tumors (16) (21), and are likely to enhance the activity of the catalytic subunit (18-20). The NOTCH1 gene was mutated in two tumors and at least one of these was inactivating (a 1 bp deletion), consistent with the recently described tumor suppressor role for this gene (22). Finally, the IDH1 (isocitrate dehydrogenase 1) gene was mutated in all seven tumors at the same residue, resulting in an amino acid substitution of His for Arg at codon 132. A high frequency of IDH1 mutations in ODs has been previously documented (23), (24) and shown to produce neo-enzymatic activity resulting in the abnormal production of 2-hydroxyglutarate (25).

Example 3

One of the major goals of this study was the investigation of the target gene(s) on chromosome 1 or 19. By analogy with other tumor suppressor genes (26), (27) we expected that the residual copy of the target gene(s) would contain mutations in most tumors with LOH of the relevant region. On chromosome 1p, there were eight somatically mutated genes, but only two with mutations in more than one tumor: FUBP1 (Far Upstream Element [FUSE] Binding Protein 1) and NOTCH2 (FIG. 5; Table s2). On chromosome 19q, there were three genetically altered genes identified, two of which were mutated in a single tumor each. The third, CIC (homolog of the *Drosophila* capicua gene), was mutated in six of the seven tumors. In each of these six cases, the fraction of mutant alleles was high (80.5±10.7%), consistent with loss of the non-mutated allele. The mutations were confirmed to be homozygous by Sanger sequencing (FIG. 2A).

Example 4

To validate these results and determine the spectrum of FUBP1, NOTCH2, and CIC mutations in ODs, we examined tumor DNA from an additional 27 tumors and matched normal cells. No additional mutations of NOTCH2 were found, but FUBP1 and CIC mutations were identified in 3 and 12 of the additional cases and generally (14 of 16 mutations) appeared to be homozygous (FIG. 2B, FIG. 6; Table s3). The probability that these mutations were passengers rather than drivers was <10$^{-8}$ for both genes (binomial test, (28). All FUBP1 mutations and more than 25% of the CIC mutations were predicted to inactivate their encoded proteins, as they altered splice sites, produced stop codons, or generated out-of-frame insertions or deletions (FIG. 2B and FIG. 6; Table s3). This type of mutational pattern is routinely observed in tumor suppressor genes such as TP53 or FBXW7 (41) but is never observed in bona fide oncogenes.

Example 5

Materials and Methods
Preparation of Illumina Genomic DNA Libraries

Fresh-frozen surgically resected tumor and matched blood were obtained from patients under an Institutional Review Board protocol. Tumor tissue was analyzed by frozen section histology to estimate neoplastic cellularity. Genomic DNA libraries were prepared following Illumina's (Illumina, San Diego, Calif.) suggested protocol with the following modifications. (1) 1-3 micrograms (μg) of genomic DNA from tumor or lymphocytes in 100 microliters (μl) of TE was fragmented in a Covaris sonicator (Covaris, Woburn, Mass.) to a size of 100-500 bp. To remove fragments shorter than 150 bp, DNA was mixed with 25 μl of 5× Phusion HF buffer, 416 μl of ddH2O, and 84 μl of NT binding buffer and loaded into NucleoSpin column (cat #636972. Clontech, Mountain View, Calif.). The column was centrifuged at 14000 g in a desktop centrifuge for 1 min, washed once with 600 μl of wash buffer (NT3 from Clontech), and centrifuged again for 2 min to dry completely. DNA was eluted in 45 μl of elution buffer included in the kit. (2) Purified, fragmented DNA was mixed with 40 μl of H2O, 10 μl of End Repair Reaction Buffer, 5 µl of End Repair Enzyme Mix (cat # E6050, NEB, Ipswich, Mass.). The 100 µl end-repair mixture was incubated at 20° C. for 30 min, purified by a PCR purification kit (Cat #28104, Qiagen) and eluted with 42 µl of elution buffer (EB). (3) To A-tail, all 42 µl of end-repaired DNA was mixed with 5 µl of 10×dA Tailing Reaction Buffer and 3 µl of Klenow (exo-) (cat # E6053, NEB, Ipswich, Mass.). The 50 µl mixture was incubated at 37° C. for 30 min before DNA was purified with a MinElute PCR purification kit (Cat #28004, Qiagen). Purified DNA was eluted with 25 µl of 70° C. EB. (4) For adaptor ligation, 25 µl of A-tailed DNA was mixed with 10 µl of PE-adaptor (Illumina), 10 µl of 5× Ligation buffer and 5 µl of Quick T4 DNA ligase (cat # E6056, NEB, Ipswich, Mass.). The ligation mixture was incubated at 20° C. for 15 min. (5) To purify adaptor-ligated DNA, 50 µl of ligation mixture from step (4) was mixed with 200 µl of NT buffer and cleaned up by NucleoSpin column. DNA was eluted in 50 µl elution buffer. (6) To obtain an amplified library, ten PCRs of 50 µl each were set up, each including 29 µl of H2O, 10 µl of 5× Phusion HF buffer, 1 µl of a dNTP mix containing 10 mM of each dNTP, 2.5 µl of DMSO, 1 µl of Illumina PE primer #1, 1 µl of Illumina PE primer #2, 0.5 µl of Hotstart Phusion polymerase, and 5 µl of the DNA from step (5). The PCR program used was: 98° C. 2 minute; 6 cycles of 98° C. for 15 seconds, 65° C. for 30 seconds, 72° C. for 30 seconds; and 72° C. for 5 min. To purify the PCR product, 500 µl PCR mixture (from the ten PCR reactions) was mixed with 1000 µl NT buffer from a NucleoSpin Extract II kit and purified as described in step (1). Library DNA was eluted with 70° C. elution buffer and the DNA concentration was estimated by absorption at 260 nm.

Exome and Targeted Subgenomic DNA Capture

Human exome capture was performed following a protocol from Agilent's SureSelect Paired-End Target Enrichment System (All Exon 50 Mb kit, Agilent, Santa Clara, Calif.) with the following modifications. (1) A hybridization mixture was prepared containing 25 µl of SureSelect Hyb #1, 1 µl of SureSelect Hyb #2, 10 µl of SureSelect Hyb #3, and 13 µl of SureSelect Hyb #4. (2) 3.4 µl (0.5 µg) of the PE-library DNA described above, 2.5 µl of SureSelect Block #1, 2.5 µl of SureSelect Block #2 and 0.6 µl of Block #3; was loaded into one well in a 384-well Diamond PCR plate (cat # AB-1111, Thermo-Scientific, Lafayette, Colo.), sealed with microAmp clear adhesive film (cat #4306311; ABI, Carlsbad, Calif.) and placed in GeneAmp PCR system 9700 thermocycler (Life Sciences Inc., Carlsbad Calif.) for 5 minutes at 95° C., then held at 65° C. (with the heated lid on). (3) 25-30 µl of hybridization buffer from step (1) was heated for at least 5 minutes at 65° C. in another sealed plate with heated lid on. (4) 5 µl of SureSelect Oligo Capture Library, 1 µl of nuclease-free water, and 1 µl of diluted RNase Block (prepared by diluting RNase Block 1:1 with nuclease-free water) were mixed and heated at 65° C. for 2 minutes in another sealed 384-well plate. (5) While keeping all reactions at 65° C., 13 µl of Hybridization Buffer from Step (3) was added to the 7 µl of the SureSelect Capture Library Mix from Step (4) and then the entire contents (9 µl) of the library from Step (2). The mixture was slowly pipetted up and down 8 to 10 times. (6) The 384-well plate was scaled tightly and the hybridization mixture was incubated for 24 hours at 65° C. with a heated lid.

After hybridization, five steps were performed to recover and amplify captured DNA library: (1) Magnetic beads for recovering captured DNA: 50 µl of Dynal MyOne Streptavidin C1 magnetic beads (Cat #650.02, Invitrogen Dynal, AS Oslo, Norway) was placed in a 1.5 ml microfuge tube and vigorously resuspended on a vortex mixer. Beads were washed three times by adding 200 µl of SureSelect Binding buffer, mixed on a vortex for five seconds, and placed in a Dynal magnetic separator to remove the supernatant. After the third wash, beads were resuspended in 200 µl of SureSelect Binding buffer. (2) To bind captured DNA, the entire hybridization mixture described above (29 µl) was transferred directly from the thermocycler to the bead solution and mixed gently; the hybridization mix/bead solution was incubated in an Eppendorf thermomixer at 850 rpm for 30 minutes at room temperature. (3) To wash the beads, the supernatant was removed from the beads after applying a Dynal magnetic separator and the beads were resuspended in 500 µl SureSelect Wash Buffer #1 by mixing on a vortex mixer for 5 seconds and incubated for 15 minutes at room temperature. Wash Buffer #1 was then removed from the beads after magnetic separation. The beads were further washed three times, each with 500 µl pre-warmed SureSelect Wash Buffer #2 after incubation at 65° C. for 10 minutes. After the final wash, SureSelect Wash Buffer #2 was completely removed. (4) To elute captured DNA, the beads were suspended in 50 µl SureSelect Elution Buffer, vortex-mixed and incubated for 10 minutes at room temperature. The supernatant was removed after magnetic separation, collected in a new 1.5 ml microcentrifuge tube, and mixed with 50 µl of SureSelect Neutralization Buffer. DNA was purified with a Qiagen MinElute column and eluted in 17 µl of 70° C. EB to obtain 15 µl of captured DNA library. (5) The captured DNA library was amplified in the following way: 15 PCR reactions each containing 9.5 µl of H2O, 3 µl of 5× Phusion HF buffer, 0.3 µl of 10 mM dNTP, 0.75 µl of DMSO, 0.15 µl of Illumina PE primer #1, 0.15 µl of Illumina PE primer #2, 0.15 µl of Hotstart Phusion polymerase, and 1 µl of captured exome library were set up. The PCR program used was: 98° C. for 30 seconds; 14 cycles of 98° C. for 10 seconds, 65° C. for 30 seconds, 72° C. for 30 seconds; and 72° C. for 5 min. To purify PCR products, 225 µl PCR mixture (from 15 PCR reactions) was mixed with 450 µl NT buffer from NucleoSpin Extract II kit and purified as described above. The final library DNA was eluted with 30 µl of 70° C. elution buffer and DNA concentration was estimated by OD260 measurement.

Somatic Mutation Identification by Massively Parallel Sequencing

Captured DNA libraries were sequenced with the Illumina GAIIx/HiSeq Genome Analyzer, yielding 150 (2×75) base pairs from the final library fragments. Sequencing reads were analyzed and aligned to human genome hg18 with the Eland algorithm in CASAVA 1.7 software (Illumina). A mismatched base was identified as a mutation only when (i) it was identified by more than five distinct tags; (ii) the number of distinct tags containing a particular mismatched base was at least 20% of the total distinct tags; and (iii) it was not present in >0.1% of the tags in the matched normal sample. SNP search databases included that of the National Library Of Medicine and that of 1000 Genomes.

Evaluation of Genes in Additional Tumors and Matched Normal Controls.

The somatic mutations in CIC, FUBP1, and NOTCH2 in the Discovery set were confirmed by Sanger sequencing as described previously (1). The entire coding regions of CIC, FUBP1, and NOTCH2 were sequenced in a validation set composed of an independent series of additional oligodendrogliomas and matched controls. PCR amplification and Sanger sequencing were performed as described in T. Sjoblom et al., *Science*, 268 (2006).

REFERENCES

The disclosure of each reference cited is expressly incorporated herein.
1. S. W. Coons, P. C. Johnson, B. W. Scheithauer, A. J. Yates, D. K. Pearl, Cancer 79, 1381 (1997).
2. J. E. Bromberg, M. J. van den Bent, Oncologist 14, 155 (2009).
3. D. Maintz et al., J Neuropathol Exp Neurol 56, 1098 (1997).
4. J. S. Smith et al., J Clin Oncol 18, 636 (2000).
5. G. Cairncross, R. Jenkins, Cancer J 14, 352 (2008).
6. R. B. Jenkins et al., Cancer Res 66, 9852 (2006).
7. C. A. Griffin et al., J Neuropathol Exp Neurol 65, 988 (2006).
8. T. D. Bourne, D. Schiff, Nat Rev Neurol 6, 695.
9. A. G. Knudson, Jr., Cancer 35, 1022 (1975).
10. Materials and methods are in Example 5.
11. L. Sastre, Clin Transl Oncol 13, 301.
12. R. Xi, T. M. Kim, P. J. Park, Brief Funct Genomics 9, 405.
13. S. H. Bigner et al., Am J Pathol 155, 375 (1999).
14. Y. Jiao et al., Science 331, 1199 (2011).
15. S. Jones et al., Science 330, 228.
16. D. W. Parsons et al., Science 321, 1807 (2008).
17. Y. Samuels et al., Science 304, 554 (2004).
18. P. K. Vogt, A. G. Bader. S. Kang, Virology 344, 131 (2006).
19. L. C. Cantley, Science 296, 1655 (2002).
20. Y. Samuels, T. Waldman, Curr Top Microbiol Immunol 347, 21.
21. Cancer Genome Atlas Research Network, Nature 455, 1061 (2008).
22. X. S. Puente et al., Nature.
23. H. Yan et al., N Engl J Med 360, 765 (2009).
24. H. Yan, D. D. Bigner, V. Velculescu, D. W. Parsons, Cancer Res 69, 9157 (2009).
25. L. Dang et al., Nature 465, 966.
26. A. G. Knudson, J. Cancer Res. Clin. Oncol. 122, 135 (1996).
27. S. J. Baker et al., Science 244, 217 (1989).
28. G. Parmigiani et al., Genomics in press, (2008).
29. G. Jimenez, A. Guichet, A. Ephrussi, J. Casanova, Genes Dev 14, 224 (2000).
30. A. Garcia-Bellido. J. F. de Celis, Annu Rev Genet 26, 277 (1992).
31. F. Roch, G. Jimenez, J. Casanova, Development 129, 993 (2002).
32. L. Ajuria et al., Development 138, 915.
33. S. Astigarraga et al., Embo J 26, 668 (2007).
34. C. J. Lee, W. I. Chan, P. J. Scotting, J Neurooncol 73, 101 (2005).
35. J. V. Olsen et al., Cell 127, 635 (2006).
36. A. J. Wong et al., Proc Natl Acad Sci USA 89, 2965 (1992).
37. S. H. Bigner et al., J Neuropathol Exp Neurol 47, 191 (1988).
38. I. Vivanco, I. K. Mellinghoff, Curr Opin Oncol 22, 573.
39. R. Duncan et al., Genes Dev 8, 465 (1994).
40. H. H. Hsiao et al., Biochemistry 49, 4620 (2010).
41. http://www.sanger.ac.uk/perl/genetics/CGP/cosmic.
42. M. Kawamura-Saito et al., Hum Mol Genet 15, 2125 (2006).
43. J. Grimwood et al., Nature 428, 529 (2004).

The invention claimed is:

1. A method of identifying and treating an oligodendroglioma in a subject, comprising:
    detecting in a sample obtained from the subject a mutation in CIC, FUBP1, or both CIC and FUBP1, wherein the mutation is selected from the group consisting of: CIC (R201W), CIC (R213P), CIC (R215Q), CIC (QK1517RD), CIC (A253T), CIC (P1485L), CIC (A306T), CIC (R215W), FUBP1 (E445X), FUBP1 (E411X), and combinations thereof,
    wherein the sample comprises a brain tissue suspected of being a brain tumor, or in cells or nucleic acids shed from the brain tumor,
    identifying the subject having the mutation as having the oligodendroglioma, and
    administering an anti-tumor agent to the subject identified as having the oligodendroglioma.

2. A method of stratifying and treating a subject with a brain tumor, comprising:
    detecting in a sample obtained from the subject a mutation of CIC, wherein the mutation is selected from the group consisting of: CIC (R201W), CIC (R213P), CIC (R215Q), CIC (QK1517RD), CIC (A253T), CIC (P1485L), CIC (A306T), CIC (R215W), and combinations thereof,
    wherein the sample comprises brain tumor tissue, or cells or nucleic acids shed from the brain tumor tissue,
    stratifying the subject having the mutation by assigning the subject to a group having an oligodendroglioma that is refractory to EGFR inhibitors, and
    administering an anti-tumor agent to the stratified subject having the oligodendroglioma that is refractory to EGFR inhibitors,
    wherein the agent is not an EGFR inhibitor.

3. The method of claim 2 further comprising:
    assigning the subject stratified as having the oligodendroglioma that is refractory to EGFR inhibitors with the to a clinical trial group, wherein the clinical trial group consists of subjects whose brain tumors have the mutation.

4. The method of claim 1, wherein detecting in a sample is performed by sequencing a nucleic acid in the sample.

5. The method of claim 2, wherein detecting in a sample is performed by sequencing a nucleic acid in the sample.

6. The method of claim 1, wherein the mutation is in CIC, and the anti-tumor agent is not an EGFR inhibitor.

* * * * *

UNITED STATES PATENT AND TRADEMARK OFFICE
CERTIFICATE OF CORRECTION

PATENT NO. : 10,619,217 B2
APPLICATION NO. : 15/834886
DATED : April 14, 2020
INVENTOR(S) : Bert Vogelstein et al.

Page 1 of 1

It is certified that error appears in the above-identified patent and that said Letters Patent is hereby corrected as shown below:

In the Specification

In Column 1, Lines 3-8, replace "STATEMENT OF FEDERALLY SPONSORED RESEARCH
This invention was made with government support under Grant No. CA43460, awarded by the National Institutes of Health. The government has certain rights in the invention.", with
--STATEMENT OF FEDERALLY SPONSORED RESEARCH
This invention was made with government support under CA043460, awarded by the National Institutes of Health. The government has certain rights in the invention.--

Signed and Sealed this
Fifteenth Day of September, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 17
<212> TYPE: DNA
<213> ORGANISM: Homo sapiens

<400> SEQUENCE: 1
cgcaagatga gaagacg                                                  17
```